United States Patent
Furuhata

(10) Patent No.: US 10,419,705 B2
(45) Date of Patent: Sep. 17, 2019

(54) ENDOSCOPE IMAGE DISPLAY APPARATUS, ENDOSCOPE IMAGE DISPLAY METHOD AND ENDOSCOPE IMAGE DISPLAY PROGRAM

(71) Applicant: OLYMPUS CORPORATION, Tokyo (JP)

(72) Inventor: Tsuyoshi Furuhata, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 185 days.

(21) Appl. No.: 15/700,354

(22) Filed: Sep. 11, 2017

(65) Prior Publication Data
US 2018/0013973 A1    Jan. 11, 2018

Related U.S. Application Data

(63) Continuation of application No. PCT/JP2016/051845, filed on Jan. 22, 2016.

(30) Foreign Application Priority Data

Mar. 13, 2015  (JP) ................................ 2015-051181

(51) Int. Cl.
*H04N 5/44* (2011.01)
*G06T 7/593* (2017.01)
(Continued)

(52) U.S. Cl.
CPC ....... *H04N 5/4403* (2013.01); *A61B 1/00009* (2013.01); *G06T 7/593* (2017.01);
(Continued)

(58) Field of Classification Search
CPC .............. H04N 5/4403; H04N 13/239; H04N 5/23229; H04N 5/44591; H04N 13/30;
(Continued)

(56) References Cited

U.S. PATENT DOCUMENTS

2006/0268257 A1   11/2006   Ogawa
2008/0015412 A1*   1/2008   Hori ................... A61B 1/00096
                                                              600/109
(Continued)

FOREIGN PATENT DOCUMENTS

JP        2006-136706 A    6/2006
JP        2006-226820 A    8/2006
(Continued)

OTHER PUBLICATIONS

International Search Report dated Apr. 12, 2016 issued in PCT/JP2016/051845.

*Primary Examiner* — Hunter B Lonsberry
(74) *Attorney, Agent, or Firm* — Scully, Scott, Murphy & Presser, P.C.

(57) ABSTRACT

An endoscope apparatus includes a display section with a touch panel having a left image display region and a right image display region and a control section. The control section is configured to perform display control so as to change, upon receiving a drag operation instruction while the left image display region selected, a position of a cursor displayed in the left image display region and the right image display region by an amount of variation da, and change, upon receiving a drag operation instruction while the right image display region selected, the position of the cursor displayed in the left image display region and right image display region by an amount of variation db.

23 Claims, 11 Drawing Sheets

(51) Int. Cl.
*H04N 5/232* (2006.01)
*H04N 5/445* (2011.01)
*A61B 1/00* (2006.01)
*H04N 13/239* (2018.01)
*H04N 5/225* (2006.01)
*H04N 13/30* (2018.01)

(52) U.S. Cl.
CPC ..... *H04N 5/23229* (2013.01); *H04N 5/44591* (2013.01); *H04N 13/239* (2018.05); *G06T 2200/24* (2013.01); *G06T 2207/10012* (2013.01); *G06T 2207/10068* (2013.01); *H04N 5/44513* (2013.01); *H04N 13/30* (2018.05); *H04N 2005/2255* (2013.01); *H04N 2005/443* (2013.01); *H04N 2005/4412* (2013.01); *H04N 2005/4432* (2013.01)

(58) Field of Classification Search
CPC ....... H04N 5/44513; H04N 2005/2255; H04N 2005/4412; H04N 2005/443; G06T 7/593; G06T 2200/24; G06T 2207/10012; G06T 2207/10068; A61B 1/00009
See application file for complete search history.

(56) References Cited

U.S. PATENT DOCUMENTS

| | | | |
|---|---|---|---|
| 2009/0245600 A1 | 10/2009 | Hoffman et al. | |
| 2010/0128116 A1* | 5/2010 | Sato | A61B 1/00045 348/65 |
| 2011/0021874 A1 | 1/2011 | Ogawa | |
| 2011/0178371 A1* | 7/2011 | Nakano | A61B 1/05 600/117 |
| 2012/0154564 A1 | 6/2012 | Hoffman et al. | |
| 2014/0066703 A1* | 3/2014 | Blumenkranz | A61B 1/00154 600/103 |
| 2015/0187067 A1* | 7/2015 | Bendall | G06F 3/04847 382/141 |

FOREIGN PATENT DOCUMENTS

| | | |
|---|---|---|
| JP | 2011-027997 A | 2/2011 |
| JP | 2013-137466 A | 7/2013 |
| JP | 2013-218517 A | 10/2013 |
| WO | WO 2013/099305 A1 | 7/2013 |

* cited by examiner

ENDOSCOPE IMAGE DISPLAY APPARATUS, ENDOSCOPE IMAGE DISPLAY METHOD AND ENDOSCOPE IMAGE DISPLAY PROGRAM

CROSS REFERENCE TO RELATED APPLICATION

This application is a continuation application of PCT/JP2016/051845 filed on Jan. 22, 2016 and claims benefit of Japanese Application No. 2015-051181 filed in Japan on Mar. 13, 2015, the entire contents of which are incorporated herein by this reference.

BACKGROUND OF THE INVENTION

1. Field of the Invention

The present invention relates to an endoscope image display apparatus, an endoscope image display method and an endoscope image display program, and more particularly, to an endoscope image display apparatus, an endoscope image display method and an endoscope image display program that display at least two endoscope images.

2. Description of the Related Art

Conventionally, endoscope apparatuses are widely used in an industrial field and a medical field. With an endoscope apparatus, an endoscope image of an object obtained through an observation window provided at a distal end portion of an insertion portion is displayed on a monitor, a user who is an inspector can inspect the object while watching the monitor and can also record the endoscope image in a storage apparatus.

Various types of endoscope apparatuses are known, and, for example, endoscopes including a stereo measuring function are available. Use of an endoscope apparatus including a stereo measuring function makes it possible to measure a distance from a distal end of an insertion portion to a specified point on an object or measure a distance between two points specified on the object.

However, car navigation systems, game machines or the like including a display apparatus with a touch panel are becoming widespread recently and users can select a function on a menu screen, move a position of a cursor on the screen or change a display range of the screen by only touching the screen of the display apparatus with a finger.

Furthermore, various ideas are being proposed to improve operability of apparatuses including a display apparatus with a touch panel. For example, Japanese Patent Application Laid-Open Publication No. 2006-226820 proposes a navigation apparatus with a touch panel which allows a scrolling speed to be arbitrarily and freely changed. The proposed navigation apparatus displays a scrolling speed specifying icon on a screen as a speed mark and the user touches the icon, gives an instruction, and can thereby change the scrolling speed when scrolling a map to a desired speed.

Since endoscope apparatuses are basically used for various inspections or various measurements, when specifying points on an object displayed on a screen of a display apparatus as measuring points, the user is required to carefully operate an operation device such as a joystick.

Similarly, in a conventional endoscope apparatus, a display range of an endoscope image on a screen of a display apparatus can be changed by a zoom function or the like, and the user needs to carefully operate an operation device such as a joystick to accurately change the display range and the user is required to perform complicated operation.

The aforementioned display apparatus with a touch panel is also applicable to an endoscope apparatus. The display apparatus with a touch panel facilitates a selection of a function or the like on a menu screen, and thereby provides excellent operability to users.

SUMMARY OF THE INVENTION

According to an aspect of the present invention, it is possible to provide an endoscope image display apparatus including a display apparatus including a first image display region and a second image display region configured to display an endoscope image, a selection section configured to select one of the first image display region and the second image display region, and a display control section configured to perform display control so as to change, upon receiving a first operation instruction while the first image display region is selected by the selection section, a position of a mark or a display range of an image displayed in the first image display region and the second image display region, by a first amount of variation, and change, upon receiving a second operation instruction while the second image display region is selected by the selection section, the position of the mark or the display range of the image displayed in the first image display region and the second image display region, by a second amount of variation which is different from the first amount of variation.

According to another aspect of the present invention, it is possible to provide an endoscope image display method including selecting, in a display apparatus including a first image display region and a second image display region configured to display an endoscope image, one of the first image display region and the second image display region, and performing display control so as to change, upon receiving a first operation instruction while the first image display region is selected, a position of a mark or a display range of an image displayed in the first image display region and the second image display region, by a first amount of variation, and change, upon receiving a second operation instruction while the second image display region is selected, the position of the mark or the display range of the image displayed in the first image display region and the second image display region, by a second amount of variation which is different from the first amount of variation.

According to a further aspect of the present invention, it is possible to provide an endoscope image display program in a display apparatus including a first image display region and a second image display region configured to display an endoscope image, the program being configured to display the first image display region and the second image display region, the program causing a computer to carry out a function of selecting, one of the first image display region and the second image display region, and a function of performing display control so as to change, upon receiving a first operation instruction while the first image display region is selected, a position of a mark or a display range of an image displayed in the first image display region and the second image display region, by a first amount of variation in the first image display region, and change, upon receiving a second operation instruction while the second image display region is selected, the position of the mark or the display range of the image displayed in the first image display region and the second image display region, by a second amount of variation which is different from the first amount of variation in the second image display region.

DETAILED DESCRIPTION OF THE PREFERRED EMBODIMENTS

Hereinafter, embodiments of the present invention will be described with reference to the accompanying drawings.

First Embodiment (Configuration)

Figure 1:
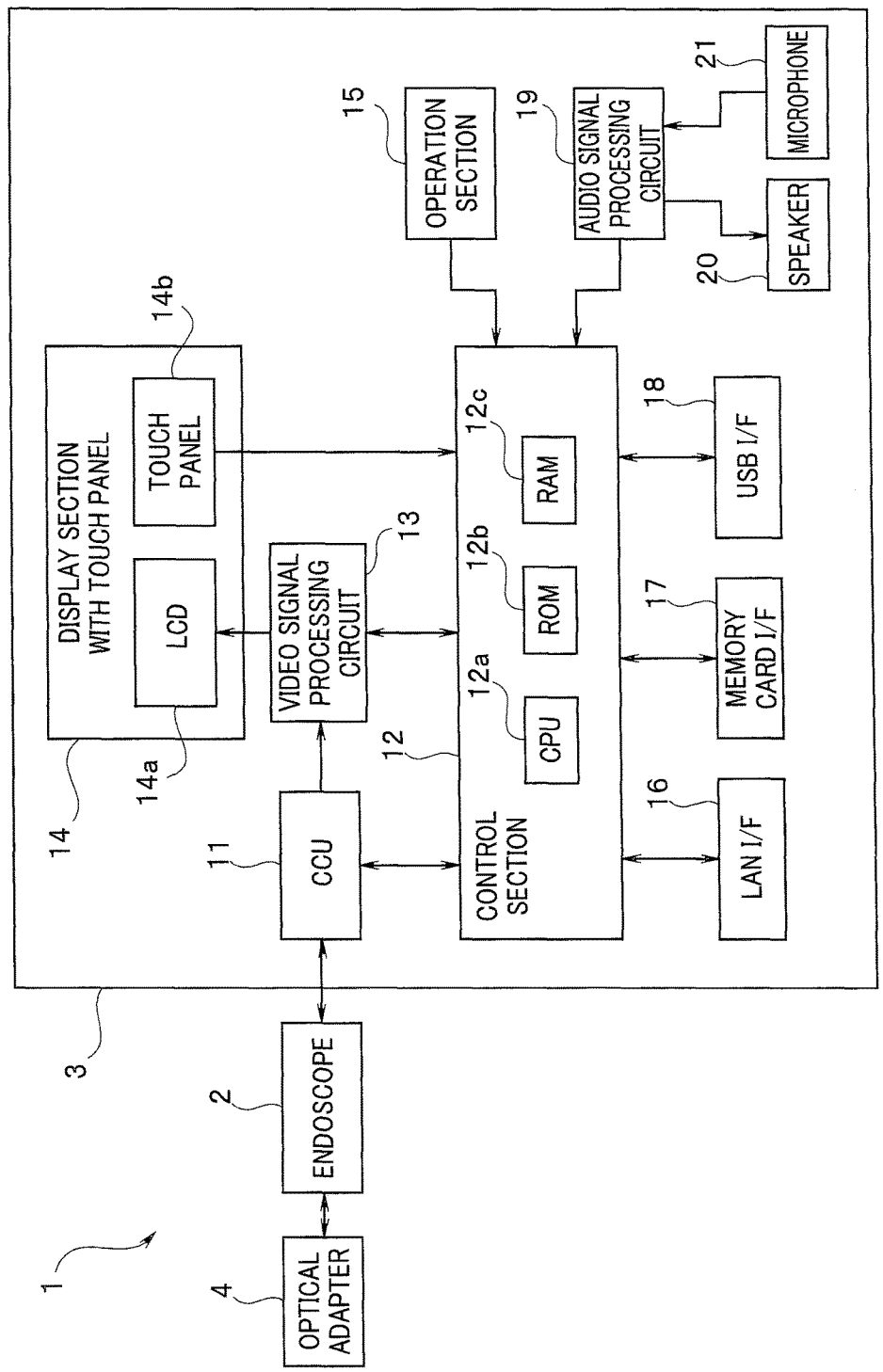
FIG. 1 is a block diagram illustrating a configuration of an endoscope apparatus according to a first embodiment of the present invention.

FIG. 1 is a block diagram illustrating a configuration of an endoscope apparatus according to a first embodiment. An endoscope apparatus 1 is constructed of an endoscope 2 and an apparatus body 3 to which the endoscope 2 is connected. The endoscope 2 is configured to be detachable from the apparatus body 3. The endoscope 2 outputs to the apparatus body 3, an image pickup signal of an object obtained through an observation window provided at a distal end portion of an insertion portion.

The endoscope apparatus 1 includes a stereo measurement function in addition to a normal observation function. Accordingly, the endoscope 2 includes an insertion portion which is not shown and an optical adapter 4 used for stereo measurement is detachably attached to a distal end portion of the insertion portion. The optical adapter 4 includes two observation windows and gives two optical images of an object having parallax with respect to each other to an image pickup surface of an image pickup device of the insertion portion of the endoscope 2. The optical adapter 4 includes a contact (not shown) to allow the endoscope 2 or the apparatus body 3 to detect that the optical adapter 4 is attached to the distal end of the insertion portion of the endoscope 2.

The apparatus body 3 is constructed of a camera control unit (hereinafter referred to as "CCU") 11, a control section 12, a video signal processing circuit 13, a display section with a touch panel (hereinafter referred to as "display section") 14, an operation section 15, a LAN interface (hereinafter abbreviated as "LAN I/F") 16, a memory card interface (hereinafter abbreviated as "memory card I/F") 17, a USB interface (hereinafter abbreviated as "USB I/F") 18, an audio signal processing circuit 19, a speaker 20, and a microphone 21.

Under the control of the control section 12, the CCU 11 drives an image pickup device (not shown) of the endoscope 2, receives an image pickup signal outputted from the image pickup device and outputs the image pickup signal to the video signal processing circuit 13.

The control section 12 receives signals from various circuits in the apparatus body 3 and also outputs control signals to the various circuits. The control section 12 includes a central processing unit (hereinafter referred to as "CPU") 12a, a ROM 12b and a RAM 12c.

The ROM 12b stores various programs and various types of setting data. The various types of setting data also include amounts of cursor variations da and db, which will be described later. The amounts of variations da and db here are amounts corresponding to a unit moving distance of a finger F when it is touching an LCD 14a (that is, a touch panel) during a drag operation which will be described later. That is each amount of variation da or db is defined as a function of the moving distance of the finger F on the LCD 14a. Note that each amount of variation da or db may also be defined as a function of a moving speed of the finger F on the LCD 14a.

Furthermore, the control section 12 can determine whether or not the optical adapter 4 is attached to the distal end of the insertion portion of the endoscope 2 based on a conduction state signal of the contact of the optical adapter 4 via the endoscope 2.

The video signal processing circuit 13 processes the image pickup signal from the CCU 11, generates an image signal and outputs the image signal to the display section 14. Under the control of the control section 12, the video signal processing circuit 13 executes image processing corresponding to various functions. When a stereo measurement function is executed, the video signal processing circuit 13 generates two endoscope images having parallax with respect to each other and outputs the two endoscope images to the display section 14. That is, the endoscope apparatus 1 is an endoscope image display apparatus.

The display section 14 includes a liquid crystal display device (LCD) 14a and a touch panel 14b. The touch panel 14b is, for example, an electrostatic touch panel and is provided in close contact on a display screen of the liquid crystal display device 14a. A position signal from the touch panel 14b is outputted to the control section 12.

The operation section 15 includes a plurality of operation devices such as a freeze button, a release button, a joystick, a zoom operation button and a menu button.

The LAN I/F 16 is an interface for connection with a local area network (hereinafter referred to as "LAN"). The endoscope apparatus 1 can communicate with external devices connected to the LAN via the LAN I/F 16.

The memory card I/F 17 is an interface for mounting a memory card as a storage medium. The endoscope apparatus 1 can record an endoscope image into the memory card and read data from the memory card via the memory card I/F 17.

The USB I/F 18 is an interface for connection of a USB (universal serial bus) cable or USB devices. The endoscope apparatus 1 can record an endoscope image into a USB device or read data from the USB device via the USB I/F 18.

Under the control of the control section 12, the audio signal processing circuit 19 processes an audio signal from the control section 12, outputs audio from the speaker 20, processes an audio signal from the microphone 21 and outputs the audio signal to the control section 12. The endoscope apparatus 1 can also record and reproduce audio together with an endoscope image.

The user who is an inspector can execute various functions of the endoscope apparatus 1 by operating the touch panel 14b or the operation section 15. The control section 12 reads a predetermined program from the ROM 12b according to a command instructed from the touch panel 14b or the operation section 15, executes the program while using the RAM 12c as a work area, and can thereby display an endoscope image on the LCD 14a, record the endoscope image obtained in the memory card or the like. Furthermore, the user attaches the optical adapter 4 to the distal end portion of the insertion portion of the endoscope 2, selects a desired command from a menu screen displayed on a screen of the LCD 14a, instructs execution of the command, and can thereby cause the endoscope apparatus 1 to also execute a stereo measurement function.

(Configuration of Stereo Live Image)

The following is a description of an endoscope image displayed on the display section 14 when the stereo measurement function is executed.

Figure 2A:
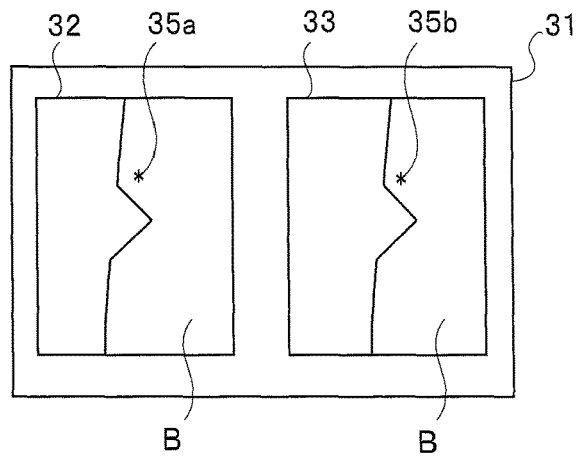
FIG. 2A is a diagram illustrating an example of a stereo live image displayed on a display section 14 in a stereo measurement mode according to the first embodiment of the present invention.
Figure 2B:
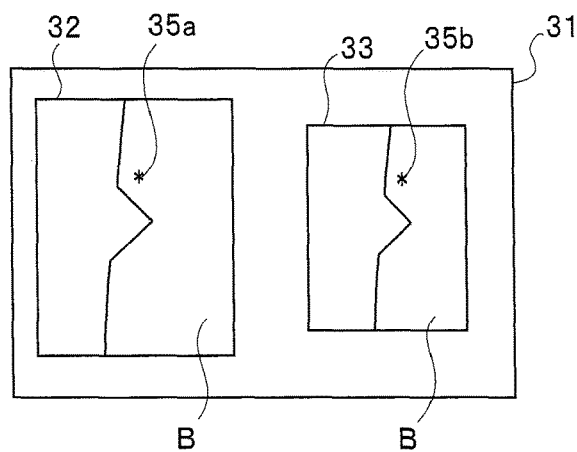
FIG. 2B is a diagram illustrating another example of the stereo live image displayed on the display section 14 in the stereo measurement mode according to the first embodiment of the present invention.
Figure 2C:
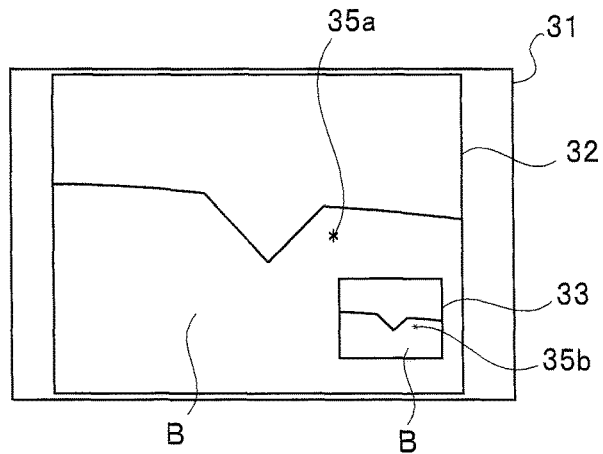
FIG. 2C is a diagram illustrating a further example of the stereo live image displayed on the display section 14 in the stereo measurement mode according to the first embodiment of the present invention.

FIG. 2A to FIG. 2C are diagrams illustrating examples of stereo live images displayed on the display section 14 in a stereo measurement mode. A screen 31 in FIG. 2A is a graphical user interface (GUI) that includes two image display regions 32 and 33 on which a stereo live image is displayed. The screen 31 displayed on the LCD 14a includes two image display regions that display two images: a left eye image and a right eye image. The display section 14 is a display apparatus that includes a left image display region 32 and a right image display region 33 configured to display an endoscope image.

Of the two image display regions, the left image display region 32 displays a left eye image and the right image display region 33 displays a right eye image. Through the optical adapter 4, the endoscope 2 generates an image pickup signal including the left and right images, and the apparatus body 3 generates the left eye image and the right eye image from the received image pickup signal and displays the images on the LCD 14a.

Note that although the left image display region 32 and the right image display region 33 are displayed on one display section of the LCD 14a of the display section 14 here, the left image display region 32 and the right image display region 33 may be displayed on different display apparatuses using two display apparatuses.

Furthermore, the left image display region 32 and the right image display region 33 need not have the same size. For example, as another example shown in FIG. 2B, the left image display region 32 may be displayed in a larger size on the screen 31 and the right image display region 33 may be displayed in a smaller size as a confirmation image.

Furthermore, as another example shown in FIG. 2C, the left image display region 32 and the right image display region 33 may be rotated by 90 degrees, the left image display region 32 may be enlarged in accordance with the screen 31 and the right image display region 33 may be displayed in a smaller size on the left image display region 32 as a confirmation image.

In the stereo measurement mode, the user can specify a measurement point. For example, by causing a cursor to be displayed as a mark to specify a measurement point on a screen, the user may perform a drag operation or the like with a finger on the touch panel 14b to move the cursor toward a desired position, and then specify the measurement point. The user can move both a left eye image cursor 35a displayed in the left image display region 32 and a right eye image cursor 35b displayed in the right image display region 33.

Hereinafter, the present embodiment will be described by taking a case where the user moves the cursor through a drag operation whereby the user does a long push of the cursor to be moved in the left image display region 32 or the right image display region 33 with the finger and then touches and moves the cursor in a desired direction. The cursor may also be moved, for example, by double tapping and specifying the cursor to be moved on the screen, then doing a swipe operation (operation of moving the cursor in a desired direction while touching the screen with the finger without specifying the location to be touched) on the screen or a flicking operation (operation of moving the cursor with sweeping motion over a short distance) or the like.

In FIG. 2A to FIG. 2C, the cursors 35a and 35b which are measurement point specifying marks are displayed in the image display regions 32 and 33 respectively. In FIG. 2A to FIG. 2C, part of a blade B in a jet engine is displayed on the LCD 14a.

The endoscope image displayed in the left image display region 32 and the endoscope image displayed in the right image display region 33 are left and right endoscope images for stereo measurement and are images having parallax with respect to each other.

Positions of the cursor 35a and the cursor 35b are displayed at positions corresponding to the parallax between the two endoscope images. Therefore, when the position of the cursor 35a in the left image display region 32 is moved, the position of the cursor 35b in the right image display region 33 is also moved, and the position of the cursor 35b is a position corresponding to the position on the object shown by the cursor 35a, where the position in the right eye image is calculated through matching processing. Similarly, when the position of the cursor 35b in the right image display region 33 is moved, the position of the cursor 35*a* in the left image display region 32 is also moved, and the position of the cursor 35*a* is a position corresponding to the position on the object shown by the cursor 35*b*, where the position in the left eye image is calculated through matching processing.

Note that a case will be described below as an example where one measurement point is specified, and two measurement points are specified when a distance between two points is measured.

(Operation)

Figure 3:
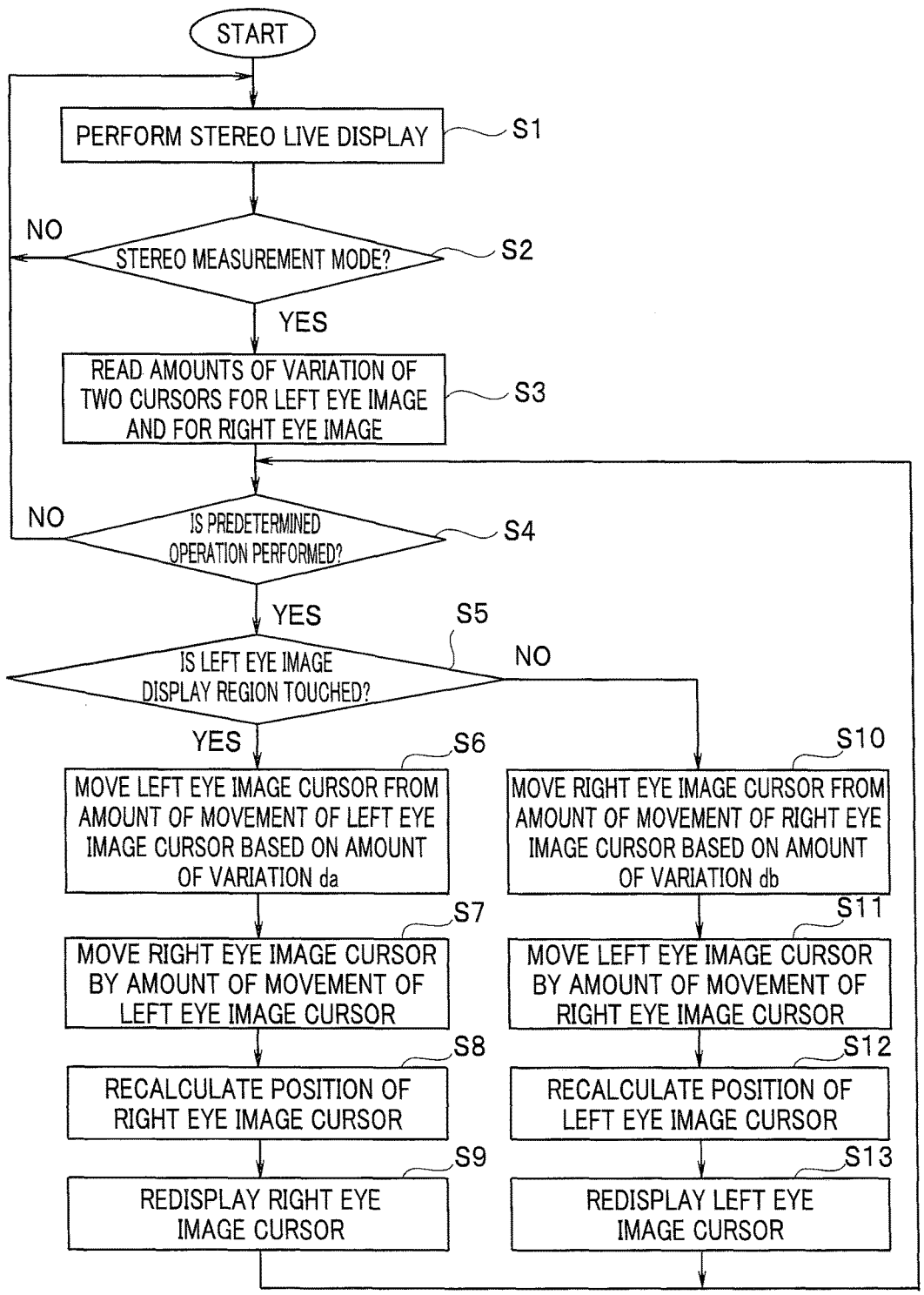
FIG. 3 is a flowchart illustrating a flow example of cursor display processing in the stereo measurement mode according to the first embodiment of the present invention.

Next, operation of the endoscope apparatus 1 according to the present embodiment will be described. FIG. 3 is a flowchart illustrating a flow example of cursor display processing in the stereo measurement mode. The processing in FIG. 3 is executed when the optical adapter 4 for stereo measurement is attached to the distal end portion of the insertion portion and the CPU 12*a* of the control section 12 reads and executes a cursor display processing program from the ROM 12*b*.

When the optical adapter 4 is attached, the control section 12 outputs an instruction to the video signal processing circuit 13 and causes the LCD 14*a* to display stereo live images as shown in FIG. 2A to FIG. 2C (S1).

Next, the control section 12 determines whether or not the stereo measurement mode is set (S2). The stereo measurement mode is set by the user selecting the stereo measurement mode from the menu screen.

When the stereo measurement mode is not set (S2: NO), the process returns to S1. When the stereo measurement mode is set (S2: YES), the control section 12 reads information on an amount of variation da of the left eye image cursor 35*a* and an amount of variation db of the right eye image cursor 35*b* from the ROM 12*b*.

The control section 12 determines whether or not a predetermined operation on the touch panel 14*b* is performed (S4). When no predetermined operation on the touch panel 14*b* is performed, the process returns to S1. The predetermined operation here refers to a drag operation of moving the finger F after a long push. That is, the control section 12 determines whether or not the drag operation is performed by moving the finger F over the touch panel 14*b* while touching the left eye image cursor 35*a* or the right eye image cursor 35*b* with the finger F.

When the predetermined operation on the touch panel 14*b* is performed (S4: YES), the control section 12 determines whether or not the operation is an operation performed on the left image display region 32 (S5).

Thus, the processes in S4 and S5 constitute a selection section that selects one of the left image display region 32 and the right image display region 33. That is, one of the left image display region 32 and the right image display region 33 is selected by touching the cursor 35*a*, 35*b* or the like.

Note that one of the left image display region 32 and the right image display region 33 may also be selected by touching the image display region to be selected or through a selection on the menu screen. In that case, since one of the left image display region 32 and the right image display region 33 is selected by touching the image display region to be selected or according to a result of selection on the menu screen, touch detection processing on the image display region to be selected and selection instruction input processing using the menu screen and a joystick or the like constitute a selection section.

When the operation in S4 is an operation on the left eye image cursor 35*a* (S5: YES), the control section 12 causes the left eye image cursor 35*a* to move within the left image display region 32 based on the amount of variation da from a moving amount of the cursor 35*a* (that is, the distance the cursor 35*a* is moved on the display section 14 through a drag operation) (S6).

Figure 4:
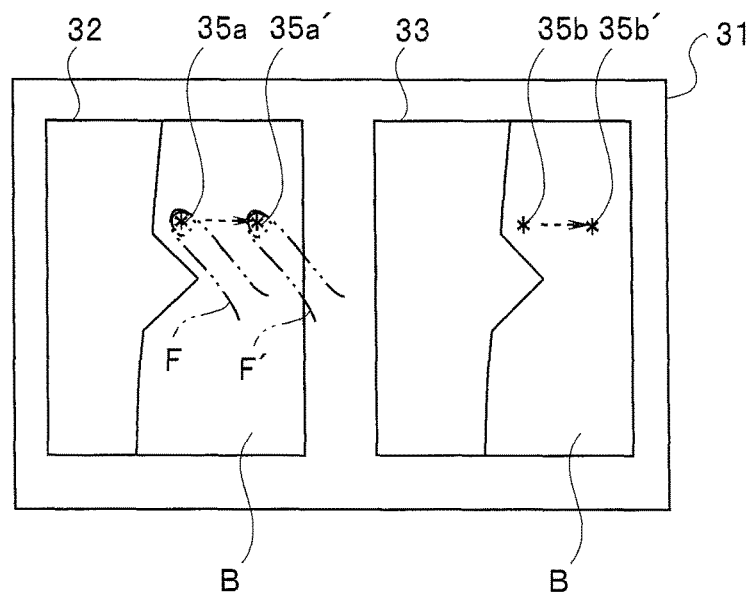
FIG. 4 is a diagram illustrating a user's finger F touching a left eye image cursor 35a according to the first embodiment of the present invention.

FIG. 4 is a diagram illustrating the user's finger F touching the left eye image cursor 35*a*. From the state in which the finger F is touching the touch panel 14*b*, the user performs a drag operation of moving the left eye image cursor 35*a* in a desired direction. Since a change of the position of the finger F by the drag operation is inputted to the control section 12, the control section 12 can calculate the moving amount of the finger F in the drag operation.

For example, suppose a case where the user drags the finger F toward a direction shown by a dotted line in FIG. 4 as the desired direction of moving the left eye image cursor 35*a*. The finger F after the movement is assumed to be a finger F'. In S6, the control section 12 causes the left eye image cursor 35*a* to move toward the drag direction (direction shown by the dotted line) within the left image display region 32 by an amount determined from the moving distance of the finger F based on the amount of variation da. For example, when the amount of variation da is set to 1 cm on the LCD 14*a* and the finger F is moved by 1 cm on the LCD 14*a*, if the finger F is dragged by a distance of 1 cm on the touch panel 14*b*, the left eye image cursor 35*a* is moved by 1 cm toward the drag direction on the LCD 14*a*. The cursor 35*a* after the movement is assumed to be a cursor 35*a*'.

After S6, the control section 12 causes the right eye image cursor 35*b* to move within the right image display region 33 by a distance corresponding to the moving amount of the left eye image cursor 35*a* (S7). In the above-described example, when the left eye image cursor 35*a* moves by a distance of 1 cm within the left image display region 32 on the touch panel 14*b*, the right eye image cursor 35*b* also moves by 1 cm toward the drag direction within the right image display region 33. The cursor 35*b* after the movement is assumed to be a cursor 35*b*'.

After moving the right eye image cursor 35*b* within the right image display region 33, the control section 12 recalculates the position of the right eye image cursor 35*b* within the right image display region 33 corresponding to the position of the left eye image cursor 35*a* within the left image display region 32 through matching processing (S8).

Note that although the position of the right eye image cursor 35*b* is recalculated after moving the right eye image cursor 35*b* within the right image display region 33 (S7), the right eye image cursor 35*b* may also be moved within the right image display region 33 while making a correction by recalculating the position of the right eye image cursor 35*b* in S7.

After S8, the control section 12 redisplays the right eye image cursor 35*b* at the corrected position within the recalculated right image display region 33 (S9).

After S9, the process returns to S4.

When the operation in S4 is an operation on the right eye image cursor 35*b* (S5: NO), the control section 12 causes the right eye image cursor 35*b* to move within the right image display region 33 based on the amount of variation db from the moving amount of the right eye image cursor 35*b* (that is, the distance by which the cursor 35*b* is moved by the drag operation on the display section 14) (S10).

Figure 5:
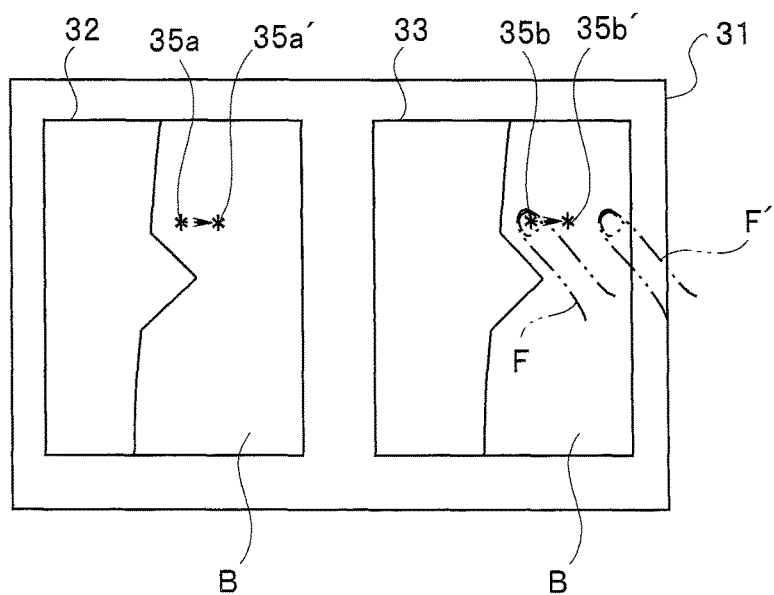
FIG. 5 is a diagram illustrating the user's finger F touching a right eye image cursor 35b according to the first embodiment of the present invention.

FIG. 5 is a diagram illustrating a state in which the user's finger F is touching the right eye image cursor 35*b*. The user performs a drag operation of moving the right eye image cursor 35*b* from the state in which the finger F is touching the touch panel 14*b* toward a desired direction.

For example, suppose a case where the user drags the finger F toward a direction shown by a dotted line in FIG. 5 as the desired direction of moving the right eye image cursor 35b. The finger F after the movement is assumed to be a finger F'. In S10, the control section 12 causes the right eye image cursor 35b to move toward the drag direction (direction shown by the dotted line) within the right image display region 33 by an amount determined from the moving distance of the finger F based on the amount of variation db. For example, when the variation db is set to 0.1 cm on the LCD 14a and the finger F is moved by 1 cm on the LCD 14a, if the finger F is dragged by a distance of 1 cm on the touch panel 14b, the right eye image cursor 35b is moved by 0.1 cm toward the drag direction on the LCD 14a. The cursor 35b after the movement is assumed to be a cursor 35b'. As shown in FIG. 5, the position of the finger F' after the movement is different from the position of the cursor 35b' after the movement.

After S10, the control section 12 moves the left eye image cursor 35a within the left image display region 32 by a distance corresponding to the moving amount of the right eye image cursor 35b (S11). In the above-described example, when the right eye image cursor 35b moves by a distance of 1 cm within the right image display region 33 on the touch panel 14b, the left eye image cursor 35a also moves by 0.1 cm toward the drag direction within the left image display region 32. The cursor 35a after the movement is assumed to be a cursor 35a'.

After causing the left eye image cursor 35a to move within the left image display region 32, the control section 12 recalculates the position of the left eye image cursor 35a within the left image display region 32 corresponding to the position of the right eye image cursor 35b within the right image display region 33 through matching processing (S12).

Note that although the position of the left eye image cursor 35a is recalculated after moving the left eye image cursor 35a within the left image display region 32 (S11), the left eye image cursor 35a may also be moved within the left image display region 32 while making a correction by recalculating the position of the left eye image cursor 35a in S11.

After S12, the control section 12 redisplays the left eye image cursor 35a at the corrected position within the recalculated left image display region 32 (S13).

After S13, the process returns to S4.

The processing in FIG. 3 ends when the user instructs to end the stereo measurement processing mode on the menu screen.

As described above, the processes in S6 to S13 constitute a display control section that performs display control such that while the left image display region 32 is selected, if a predetermined operation instruction by a drag operation is received, the positions of the respective cursors 35a and 35b as marks displayed on the left image display region 32 and the right image display region 33 are changed by the amount of variation da, and while the right image display region 33 is selected, if a predetermined operation instruction by a drag operation is received, the positions of the respective cursors 35a and 35b as marks displayed on the left image display region 32 and the right image display region 33 are changed by the amount of variation db which is different from the amount of variation da.

In the aforementioned example, since the amount of variation da is set to be greater than the amount of variation db, when the processing in FIG. 3 is repeated, the user can repeat a coarse movement to move the cursors 35a and 35b in large steps by touching the inside of the left image display region 32 and a fine movement to move the cursors 35a and 35b in small steps by touching the inside of the right image display region 33 one or more times respectively. Therefore, the user can move the cursors 35a and 35b toward a desired position speedily and accurately.

Figure 6:
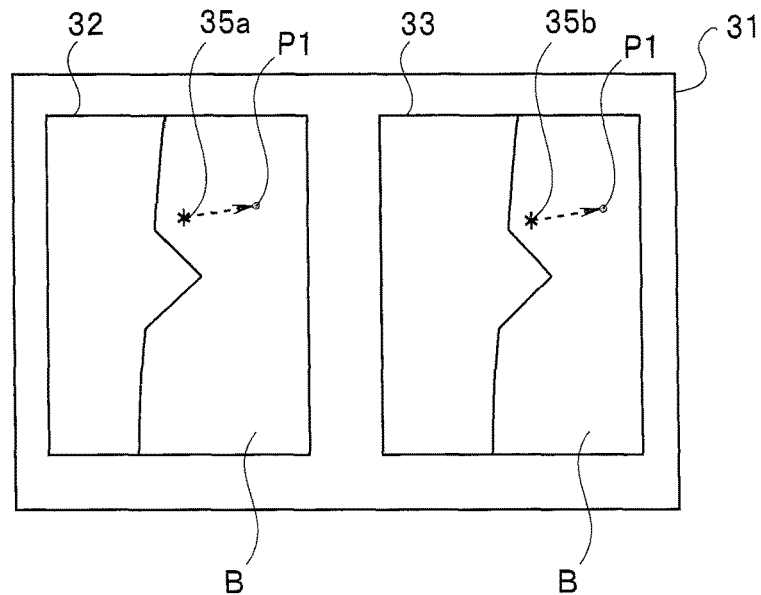
FIG. 6 is a diagram for describing a cursor movement according to the first embodiment of the present invention.

FIG. 6 is a diagram for describing a cursor movement. When the user wants to move the cursors 35a and 35b to a desired position P1, the user repeats operations of the aforementioned coarse movement and the fine movement by the aforementioned drag operation several times, and can thereby move the cursors 35a and 35b to the desired position P1 simply and speedily by a small number of operations.

Figure 7:
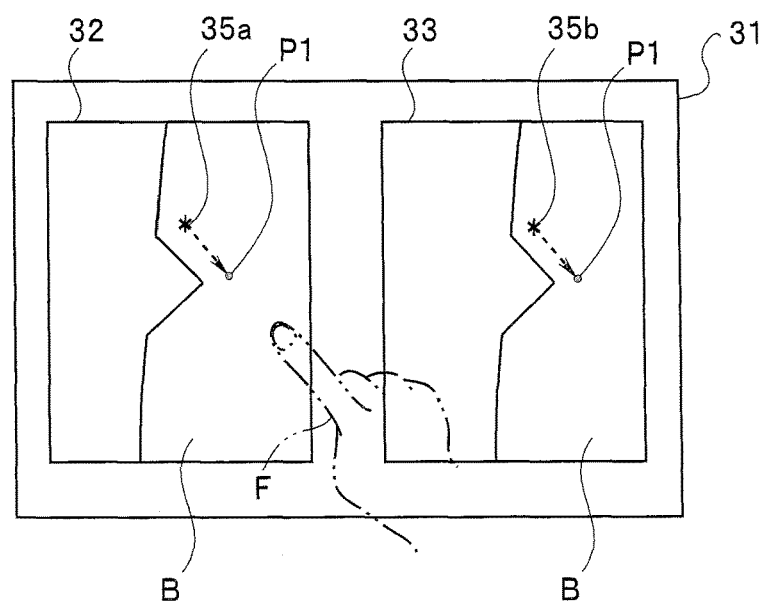
FIG. 7 is a diagram for describing another example of cursor movement according to the first embodiment of the present invention.

FIG. 7 is a diagram for describing another example of cursor movement. FIG. 7 illustrates a case using a method whereby the user moves the cursor toward a desired direction by touching an arbitrary position on the screen.

In the case of FIG. 7, when the user touches an arbitrary position with the finger F in a desired direction of moving the cursors 35a and 35b, the cursors 35a and 35b move toward the direction indicated with the finger. For example, in FIG. 7, when the finger F touches the inside of the left image display region 32 toward the desired direction of moving the cursor 35a, the cursor 35a moves toward the direction indicated with the finger F. When the cursor 35a moves up to the position of the finger F, the cursor 35a stops. If the finger F is moved while the cursor 35a is moving toward the finger F, the cursor 35a moves toward the moved finger F. If the finger F is released while the cursor 35a is moving toward the finger F, the cursor 35a stops. As the cursor 35a moves or stops, the cursor 35b also moves or stops. When the inside of the left image display region 32 is touched, the cursors 35a and 35b start a coarse movement, whereas when the inside of the right image display region 33 is touched, the cursors 35a and 35b start a fine movement.

Note that as shown in FIG. 2B or FIG. 2C, when the size of the left image display region 32 displayed on the screen 31 is different from the size of the right image display region 33, the moving amount of each cursor based on each amount of variation is changed in proportion to the difference in size between the two regions.

Note that in FIG. 7, when the finger F is moved from a state in which the finger F touches the inside of the left image display region 32 to another position in a desired direction of moving the cursor 35a, if the finger F moves beyond the left image display region 32 or if the cursor 35b in the right image display region 33 in FIG. 5 is dragged, the finger F may possibly move beyond the right image display region 33.

In such a case, when the drag operation remains in progress without the finger F being detached from the touch panel 14b, the cursors 35a and 35b are caused to move even beyond the image display region first touched with the finger F, based on the amount of variation da for the left image display region 32 first touched with the finger F or the amount of variation db for the right image display region 33. That is, when operation remains in progress beyond the image display region first touched with the finger F, the cursors 35a and 35b are moved by continuously using the value of amount of variation for the image display region first touched with the finger F.

That is, in the processes in S6 to S13, when an operation instruction given while the left image display region 32 is selected remains in progress even in a region beyond the left image display region 32, the position of the cursor 35a may be continuously changed based on the amount of variation da, and when an operation instruction given while the right image display region 33 is selected remains in progress even in a region beyond the right image display region 33, the position of the cursor 35b may be continuously changed based on the amount of variation db.

As described above, according to the aforementioned embodiment, it is possible to provide an endoscope image display apparatus capable of specifying the position of a measurement point or the like in at least two or more endoscope images speedily by a small number of operations.

Even when the cursor is being moved in one of the two image display regions on the display section 14, at least the other of the two image display regions is never hidden with the finger F or hand, and so the user can surely recognize the position of the cursor on the image display region. Furthermore, as shown in FIG. 7, when the cursor is operated by touching an arbitrary position on the screen, it is possible to recognize the positions of the cursors in the two image display regions.

Second Embodiment

The present embodiment relates to operation of enlarged and reduced display of an endoscope image. The user may want to see an enlarged view of an endoscope image or a reduced view of the whole endoscope image. Furthermore, also when specifying a measurement point, the user may want to specify the measurement point by enlarging or reducing the display range of the endoscope image. The present embodiment relates to an endoscope apparatus capable of performing operation of changing the display range of such an endoscope image speedily by a small number of operations.

Since the endoscope apparatus of the present embodiment has the same components as the components of the endoscope apparatus 1 of the first embodiment, the same components are assigned the same reference numerals, description of the components is omitted and only different components will be described.

Figure 8:
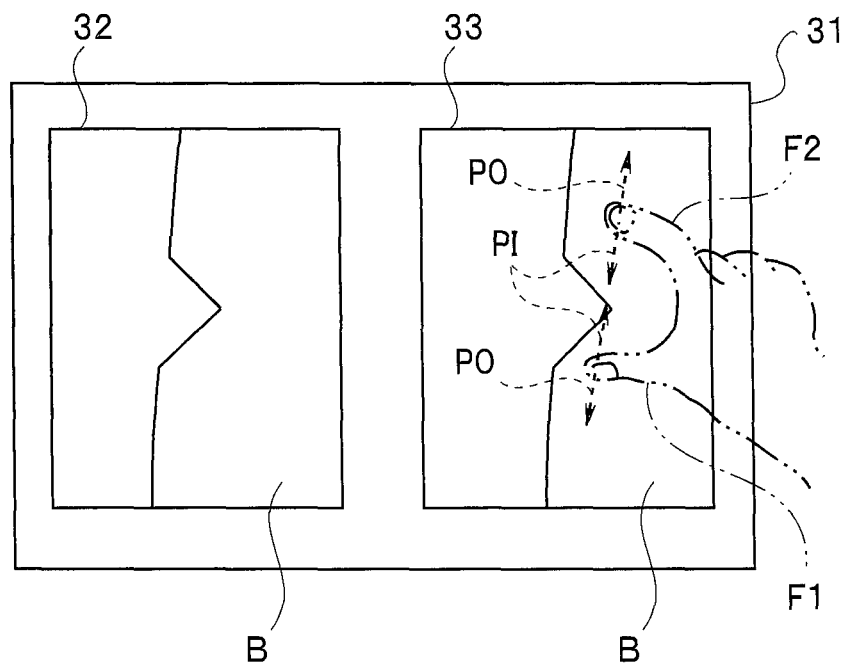
FIG. 8 is a diagram illustrating operations of enlarging and reducing an endoscope image in a stereo live image according to a second embodiment of the present invention.

FIG. 8 is a diagram illustrating operations of enlarging and reducing an endoscope image in a stereo live image. The user can zoom-out or zoom-in an endoscope image displayed in the left image display region 32 and the right image display region 33 by performing pinch-in or pinch-out operation using the two fingers F1 and F2 on the display section 14.

FIG. 8 illustrates the pinch-in or pinch-out operation carried out by the two fingers F1 and F2 in the right image display region 33. In FIG. 8, a dotted line PO denotes the pinch-out operation of increasing the distance between the two fingers F1 and F2 and a dotted line PI denotes the pinch-in operation of reducing the distance between the two fingers F1 and F2. The pinch-out operation enlarges the endoscope image, that is, carries out zoom-in and the pinch-in operation reduces the endoscope image, that is, carries out zoom-out.

According to the present embodiment, pinch-in or pinch-out operation is possible on the right image display region 33 and pinch-in or pinch-out operation is possible on the left image display region 32 as well.

However, while the zoom amount is large in the pinch-in or pinch-out operation on the left image display region 32, the zoom amount is small in the pinch-in or pinch-out operation on the right image display region 33.

For this reason, the ROM 12b stores information of amounts of zoom variations dc and dd. The amount of variation dc is an amount of variation during zooming within the left image display region 32 and the amount of variation dd is an amount of variation during zooming within the right image display region 33. Here, the amounts of variations dc and dd are amounts corresponding to changes in the distance between the fingers F1 and F2 when each finger touches the LCD 14a (that is, the touch panel) during the pinch-in or pinch-out operation. That is, each amount of variation dc or dd is defined as a function of amount of variation of the distance between the fingers F1 and F2 on the LCD 14a. Each amount of variation dc or dd is defined such that when the user carries out pinch-out operation on the left image display region 32 and the distance between F1 and F2 is changed by 1 cm, the image is enlarged 10 times, and when the user carries out pinch-out operation on the right image display region 33 and the distance between F1 and F2 is changed by 1 cm, the image is enlarged 1.1 times, for example.

Note that although the amounts of variations dc and dd are used here, a change rate may also be used. When the initial distance between the fingers F1 and F2 is L0 and the distance between the fingers F1 and F2 after the operation is L1, the change rate is expressed by L1/L0.

Figure 9:
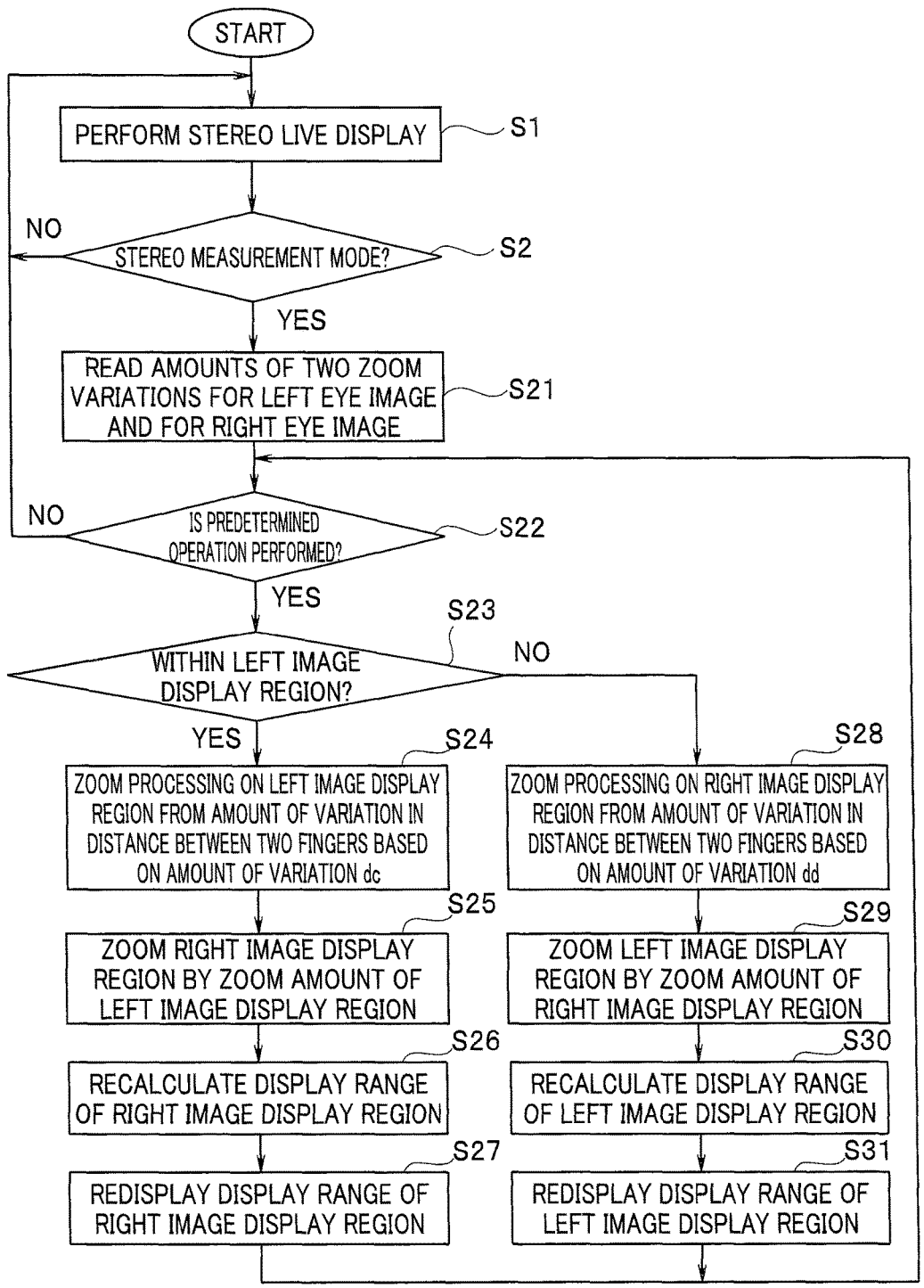
FIG. 9 is a flowchart illustrating a flow example of zoom display processing in a stereo measurement mode according to the second embodiment of the present invention.

Next, operation of the endoscope apparatus 1 of the present embodiment will be described. FIG. 9 is a flowchart illustrating a flow example of zoom display processing in a stereo measurement mode. Note that in FIG. 9, processes identical to the processes in FIG. 3 are assigned identical step numbers and description of the processes is omitted.

When the stereo measurement mode is set (S2: YES), the control section 12 reads information of the amount of variation dc which is an amount of left eye image zoom variation and the amount of variation dd which is an amount of right eye image zoom variation from the ROM 12b (S21).

The control section 12 determines whether or not a predetermined operation on the touch panel 14b is performed (S22). When no predetermined operation on the touch panel 14b is performed, the process returns to S1. The predetermined operation here is the aforementioned pinch-in or pinch-out operation. That is, it is determined whether or not pinch-in or pinch-out operation is performed within the left image display region 32 or the right image display region 33.

When the predetermined operation on the touch panel 14b is performed (S22: YES), the control section 12 determines whether or not the operation is a zoom operation caused by a pinch-in or pinch-out operation within the left image display region 32 (S23).

When the operation in S22 is a pinch-in or pinch-out operation within the left image display region 32 (S23: YES), the control section 12 performs zoom processing on the left image display region 32 from the amount of variation in the distance between the two fingers F1 and F2 in the left image display region 32 based on the amount of variation dc (S24). In the case of a pinch-in operation, the left image display region 32 is reduced, whereas in the case of a pinch-out operation, the left image display region 32 is enlarged.

After S24, the control section 12 zooms the right image display region 33 by a zoom amount of the left image display region 32 (S25). As a result, the right image display region 33 is also zoomed by the same amount as the amount of the left image display region 32.

After zooming the right image display region 33, the control section 12 recalculates the display range of the right image display region 33 corresponding to the display range of the left image display region 32 through matching processing (S26).

After S26, the control section 12 redisplays the display range of the right image display region 33 corrected by the recalculation (S27).

After S27, the process returns to S22.

When the operation in S22 is a pinch-in or pinch-out operation within the right image display region 33 (S23: NO), the control section 12 performs zoom processing on the right image display region 33 from an amount of variation in the distance between the two fingers F1 and F2 in the right image display region 33 based on the amount of variation dd (S28). In the case of a pinch-in operation, the right image display region 33 is reduced, whereas in the case of a pinch-out operation, the right image display region 33 is enlarged.

After S28, the control section 12 zooms the left image display region 32 by a zoom amount of the right image display region 33 (S29). As a result, the left image display region 32 is also zoomed by the same amount as the amount of the right image display region 33.

After zooming the left image display region 32, the control section 12 recalculates the display range of the left image display region 32 corresponding to the display range of the right image display region 33 through matching processing (S30).

After S30, the control section 12 redisplays the display range of the left image display region 32 corrected by the recalculation (S31).

After S31, the process returns to S22.

Note that the display ranges in S26 and S30 are recalculated after zooming the other corresponding image display region (S25, S29), but it is also possible, in S25 or S29, to zoom the other corresponding image display region while recalculating the display range of the other corresponding image display region.

The processing in FIG. 9 ends when the user instructs to end the stereo measurement processing mode on the menu screen.

As described above, the processes in S24 to S31 constitute a display control section that performs display control such that while the left image display region 32 is selected, if an operation instruction for zoom operation such as pinch-in or pinch-out operation is received, the display range of the left image display region 32 and the right image display region 33 is changed by the amount of variation dc, and while the right image display region 33 is selected, if an operation instruction for zoom operation is received, the display range of the left image display region 32 and the right image display region 33 is changed by the amount of variation dd which is different from the amount of variation dc.

In the aforementioned example, since the amount of variation dc is set to be greater than the amount of variation dd, when the processing in FIG. 9 is repeated, the user can repeat a coarse zoom of changing the display range of the left image display region 32 and the display range of the right image display region 33 in large steps by performing a pinch-in or pinch-out operation within the left image display region 32 and a fine zoom of changing the display range of the left image display region 32 and the display range of the right image display region 33 in small steps by performing a pinch-in or pinch-out operation within the right image display region 33, one or more times respectively. Thus, the user can zoom the display range of the left image display region 32 and the display range of the right image display region 33 to a desired size speedily and accurately.

Note that such a configuration may also be adopted in which if a pinch-out operation is performed once on the left image display region 32 or the right image display region 33, the image may be enlarged up to a maximum magnification and if a pinch-in operation is performed once, the image may be reduced down to a minimum magnification. Such a configuration enables a maximum or minimum display by one operation.

As described above, according to the endoscope apparatus of the aforementioned embodiment, it is possible to change the display range of at least two or more endoscope images displayed on a screen speedily by a small number of operations.

Third Embodiment

The present embodiment relates to the endoscope apparatus 1 that can instruct a cursor movement by a move button 41 which is an instruction button disposed in a region other than the left image display region 32, together with an immediate cursor movement by a touch operation on the left image display region 32.

Since the endoscope apparatus 1 of the present embodiment has the same components as the components of the endoscope apparatus 1 of the first embodiment and the second embodiment, the same components are assigned the same reference numerals, description of the components is omitted and only different components will be described hereinafter.

Figure 10A:
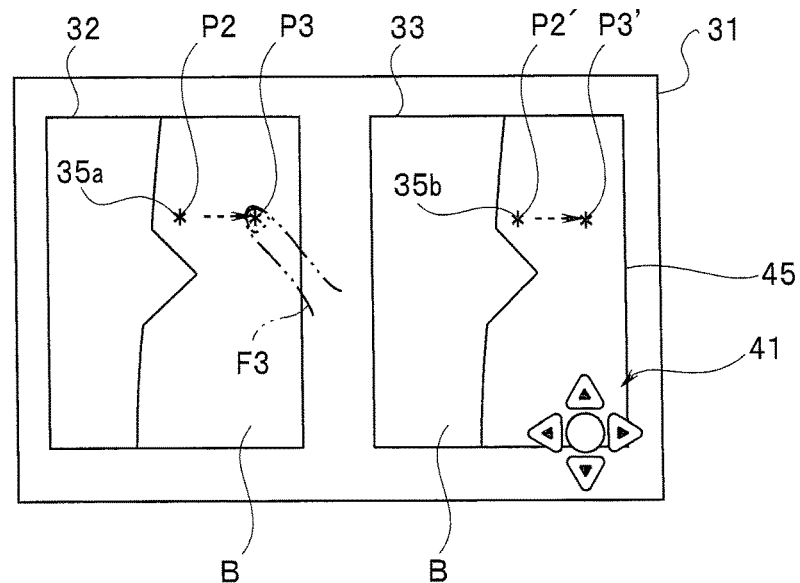
FIG. 10A is a diagram illustrating a move button displayed in a stereo measurement mode according to a third embodiment of the present invention.

FIG. 10A is a diagram illustrating a status in which a move button 41 which is an instruction button is displayed in a stereo measurement mode. The left eye image cursor 35a is displayed in the left image display region 32. The user touches with the finger, a position in the left image display region 32 to which the left eye image cursor 35a is desired to be moved, and can thereby immediately move the left eye image cursor 35a to the position touched with the finger. An amount of variation de in the left image display region 32 is an amount of difference between a position P3 touched by the user's finger and a position P2 of the left eye image cursor 35a displayed in the left image display region 32, that is a distance, and so the left eye image cursor 35a which is a mark displayed in the left image display region 32 immediately moves to the position touched with the finger. That is, in FIG. 10A, the cursor 35a of the left image display region 32 immediately moves from the position P2 to the position P3 touched with the finger.

The move button 41 which is an instruction button is displayed in a region other than the left image display region 32 to which the cursor is immediately moved by the user's touch operation. That is, in FIG. 10A, the move button 41 is disposed superimposed on part of the right image display region 33 so as to cross over a frame line part 45 of the right image display region 33 in a bottom-right corner of the right image display region 33.

At this time, the move button 41 is disposed at a position not obstructing the right eye image cursor 35b. When the movement of the right eye image cursor 35b is started, the move button 41 is hidden so as not to obstruct the display of the right eye image cursor 35b during the movement. As a result of the movement of the right eye image cursor 35b, if the move button 41 and the right eye image cursor 35b overlap each other, the move button 41 is changed to a position where it does not overlap the right eye image cursor 35b as appropriate and redisplayed.

Figure 10B:
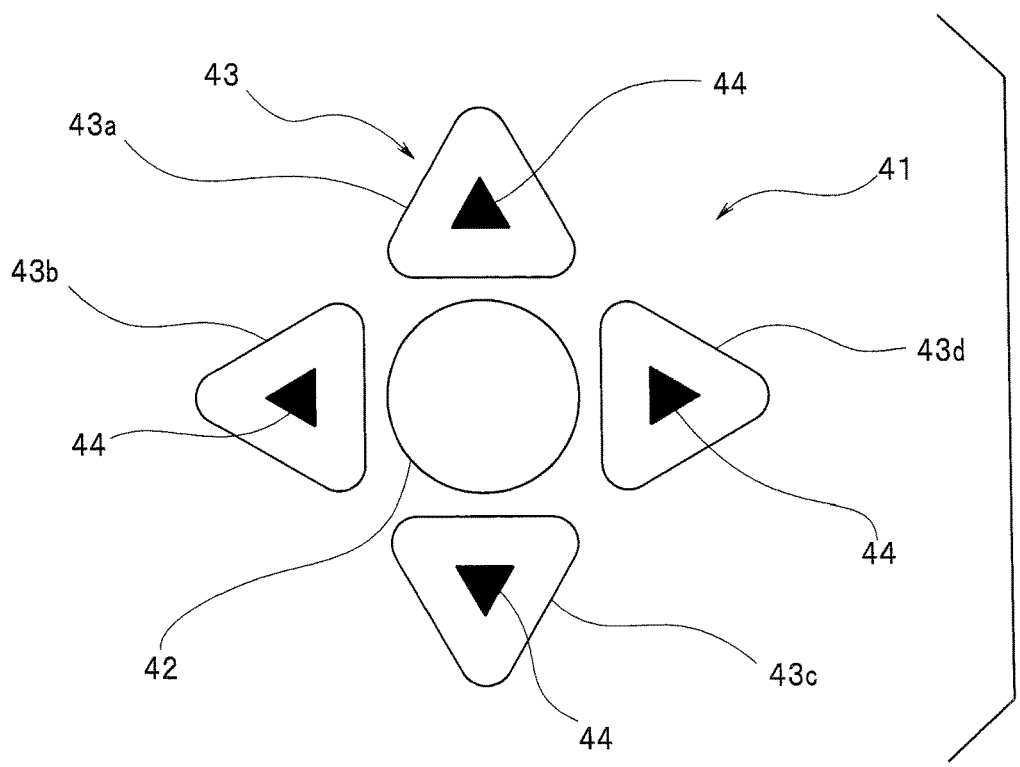
FIG. 10B is an enlarged view of the move button according to the third embodiment of the present invention.

FIG. 10B is an enlarged view of the move button 41. The move button 41 is constructed of an enter button 42, an up button 43a, a left button 43b, a down button 43c and a right button 43d. The four rounded-corner triangle buttons making up the up button 43a, the left button 43b, the down button 43c and the right button 43d have bases near the enter button, small circular parts facing the base are disposed outward, and small triangular parts 44 are included in the triangle buttons. When referring to any one of the up button 43a, the left button 43b, the down button 43c and the right button 43d or all direction buttons 43, the buttons will be referred to as "direction button(s) 43."

The direction buttons 43 and the enter button 42 are non-transparent. Therefore, in FIG. 10A, the direction buttons 43 and the enter button 42 are displayed so as to hide the image in the right image display region 33 and the frame line part 45.

The direction buttons 43 are buttons indicating a movement toward each moving direction of the cursor. The user touches with the finger, the direction button 43, and can thereby cause the cursor to move toward a direction indicated by the direction button 43.

That is, the move button 41, which is an instruction button, is a button indicating a movement of the cursor, which is a mark, and the direction button 43 is a button indicating a movement toward each moving direction of the cursor, which is the mark.

The enter button 42 is a button for giving various instructions to the endoscope apparatus 1.

The move button 41 is displayed for a predetermined display time period according to a timer, which is not shown, or the like and hidden after a lapse of a predetermined display time period. Even during display, if the position of the move button 41 is determined by the enter button 42, it may be determined that the operation of the move button 41 is completed and the move button 41 may be hidden without waiting for the predetermined display time period to pass.

The ROM 12b stores information on an amount of variation df of the right image display region 33. Here, the amount of variation df is an amount corresponding to the number of times the finger touches the direction buttons 43. That is, the amount of variation df is defined as a function of the number of times the finger touches the direction buttons 43. Note that the amount of variation df may also be defined as a function of a time period during which the finger touches the direction buttons 43.

Thus, the user can perform a coarse movement to move the cursor 35a in large steps by touching with the finger, a position in the left image display region 32 to which the left eye image cursor 35a is desired to be moved and a fine movement to move the cursor in small steps by touching with the finger, the move button 41 in the right image display region 33.

Note that the present embodiment assumes the left image display region 32 as a coarse movement region and assumes the right image display region 33 as a fine movement region, whereas on the contrary, the left image display region 32 may be assumed to be the fine movement region and the right image display region 33 may be assumed to be the coarse movement region. In that case, when the user touches the right image display region 33, the right image display region 33 is selected to be the coarse movement region, and the move button 41 for causing the cursor to perform a fine movement is disposed in a region other than the right image display region 33 (left image display region 32 or the like).

Figure 11:
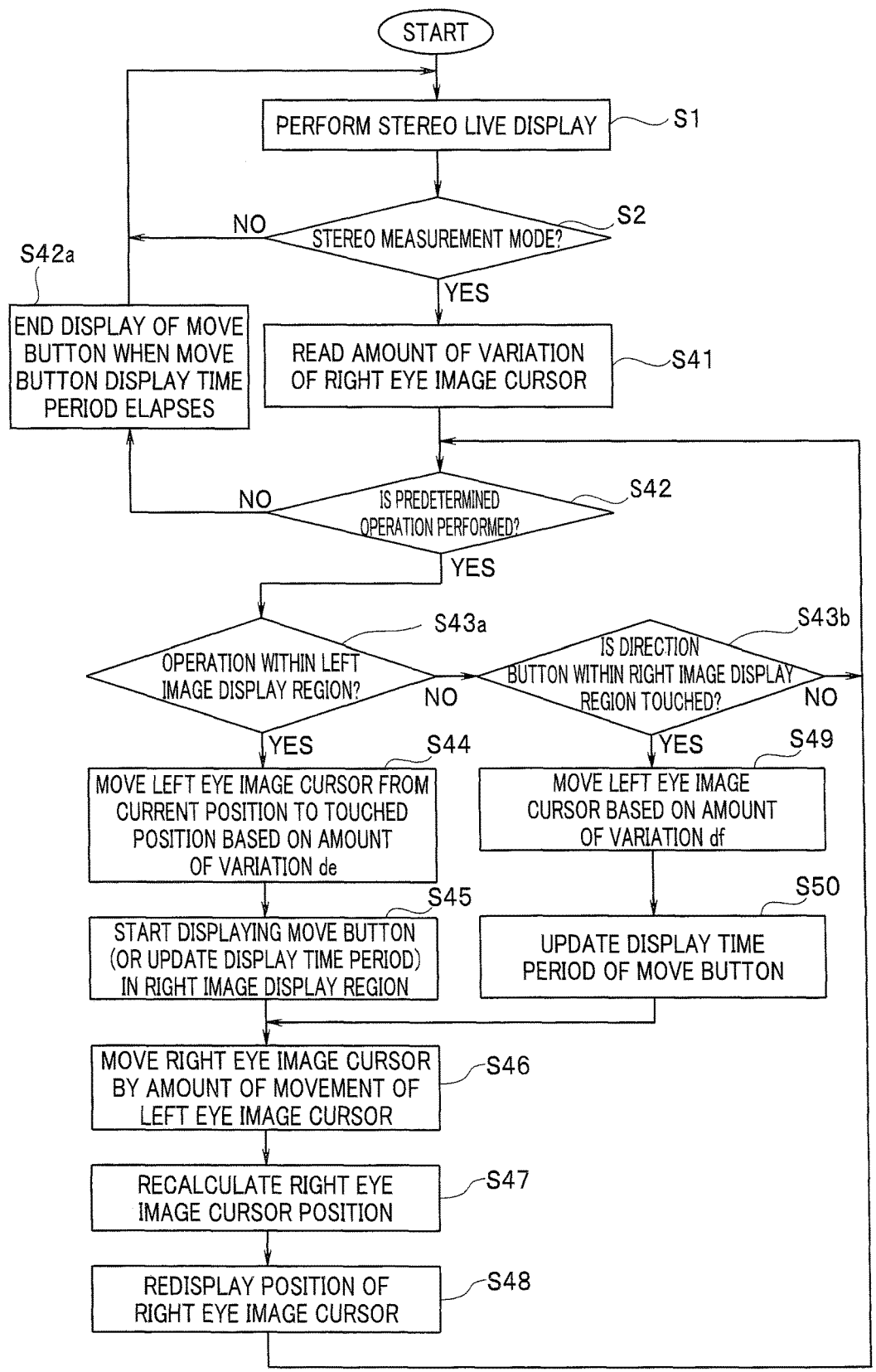
FIG. 11 is a flowchart for describing an example of cursor movement in the stereo measurement mode according to the third embodiment of the present invention.

Next, operation of the endoscope apparatus 1 according to the present embodiment will be described. FIG. 11 is a flowchart for describing an example of cursor movement in the stereo measurement mode. Note that in FIG. 11, processes identical to the processes in FIG. 3 are assigned identical step numbers and description of the processes is omitted.

When the stereo measurement mode is set (S2: YES), the control section 12 reads information of the amount of variation df of the right eye image cursor 35b from the ROM 12B (S41).

The control section 12 determines whether or not a predetermined operation on the touch panel 14b is performed. If no predetermined operation on the touch panel 14b is performed, the process proceeds to S42a (S42). The predetermined operation here is a touch operation on the touch panel 14b.

The process in S42a differs between a case where the move button 41 is hidden and a case where the move button 41 is already displayed by the process in S45 which will be described later. In S42a, the control section 12 determines whether or not the move button 41 is displayed, and if the move button 41 is already displayed and the predetermined display time period of the move button 41 elapses, the move button 41 is hidden (S42a). After S42a, the process returns to S1.

When the predetermined operation on the touch panel 14b is performed in S42, the control section 12 determines whether or not the operation is a touch operation within the left image display region 32 (S43a).

When the touch operation in S43 a is a touch operation within the left image display region 32 (S43a: YES), the control section 12 calculates an amount of difference between the position P2 of the left eye image cursor 35a and the position P3 touched with the finger as the amount of variation de and moves the cursor 35a by the amount of variation de. That is, the control section 12 moves the left eye image cursor 35a to the position P3 touched with the finger (S44).

Next, the control section 12 performs a process related to the display of move button 41. The process differs between a case where the move button 41 is hidden because of an initial process and a case where the move button 41 is already displayed through the second and subsequent processes. When the move button 41 is hidden due to the initial process or the like, the move button 41 is disposed superimposed on part of the right image display region 33 so as to cross over the frame line part 45 of the right image display region 33 in the bottom-right corner of the right image display region 33. When the move button 41 is already displayed through the second and subsequent processes, the display time period is updated so that it is extended by a predetermined time period. At this time, the control section 12 acquires the display position of the right eye image cursor 35a and if the move button 41 and right eye image cursor 35a overlap in display, the move button 41 is moved to a position where the move button 41 and the right eye image cursor 35a do not overlap, and displayed (S45).

After the process in S45, the control section 12 moves the right eye image cursor 35b by a distance corresponding to the moving amount of the left eye image cursor 35a within the right image display region 33 (S46). In the example in FIG. 10A, the left eye image cursor 35a moves from P2 to P3 and the right eye image cursor moves from P2' to P3' accordingly.

After moving the right eye image cursor 35b within the right image display region 33 (S46), the control section 12 recalculates, through matching processing, the position of the right eye image cursor 35b within the right image display region 33 corresponding to the position of the left eye image cursor 35a within the left image display region 32 (S47).

After S47, the control section 12 redisplays the right eye image cursor 35b at a corrected position within the recalculated right image display region 33 (S48).

Note that the position of the right eye image cursor 35b is recalculated after moving the right eye image cursor 35b within the right image display region 33 (S46), but the right eye image cursor 35b may also be moved within the right image display region 33 while making a correction by recalculating the position of the right eye image cursor 35b in S46.

After redisplaying the right eye image cursor 35b through the process in S48, the process returns to S42.

When the operation in S43a is not a touch operation within the left image display region 32 (S43a: NO), the control section 12 further determines whether or not the touch operation in S43a is a touch operation of the direction buttons 43 of the move button 41 within the right image display region 33 (S43b). When the touch operation in S43b is not a touch operation of the direction buttons 43 within the right image display region 33 (S43b: NO), the process returns to S42. On the other hand, when the operation in S43b is a touch operation of the direction buttons 43 within the right image display region 33 (S43b: YES), the process proceeds to S49.

The control section 12 determines which direction button 43 is touched and moves the right eye image cursor 35b within the right image display region 33 toward each direction indicated by the direction button 43 (e.g., upward direction when the up button 43a is touched) by an amount determined from the number of times the button is touched with the finger based on the amount of variation df. At this time, the control section 12 acquires a display position of the right eye image cursor 35b and if the move button 41 and the right eye image cursor 35a overlap in display, the control section 12 moves the move button 41 to a position where the move button 41 and the right eye image cursor 35a do not overlap and displays the move button 41 (S49).

After moving the cursor 35b within the right image display region 33 (S49), the control section 12 updates the display time period of the move button 41 so that it is extended (S49).

After S50, the process proceeds to S46.

The process in FIG. 11 ends when the user instructs to end the stereo measurement processing mode on the menu screen.

As described above, the processes in S44 to S50 constitute a display control section that performs display control such that while the left image display region 32 is selected, if a predetermined operation instruction by a touch operation of the left image display region 32 is received, the positions of the cursors as marks displayed on the left image display region 32 and the right image display region 33 are changed by the amount of variation de, and while the right image display region 33 is selected, if a predetermined operation instruction by a touch operation of the move button 41 is received, the positions of the cursors as marks displayed on the left image display region 32 and the right image display region 33 are changed by the amount of variation df which is different from the amount of variation de.

In the aforementioned example, the user can repeat a coarse movement to move the cursor in large steps through a touch operation on the inside of the left image display region 32 and a fine movement to move the cursor in small steps through a touch operation on the move button 41 one or more times respectively. Thus, the user can move the cursor toward a desired position speedily and accurately.

Fourth Embodiment

The present embodiment relates to an endoscope apparatus that allows a zoom button 51 which is an instruction button disposed in a region other than the left image display region 32 to instruct an operation for enlarged display or reduced display of an endoscope image together with a pinch-in or pinch-out operation on the left image display region 32.

Since the endoscope apparatus 1 of the present embodiment has the same components as the components of the endoscope apparatus 1 according to the first embodiment, the second embodiment and the third embodiment, the same components are assigned the same reference numerals, description of the components is omitted and only different components will be described.

Figure 12A:
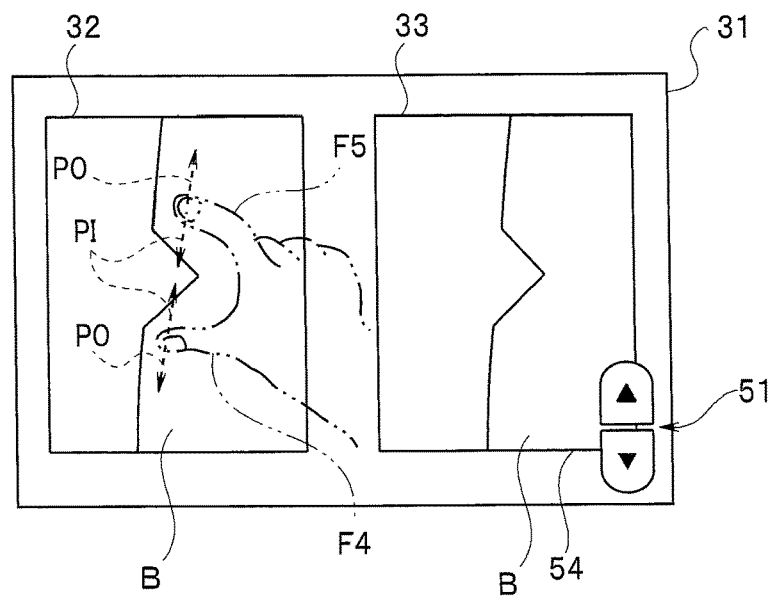
FIG. 12A is a diagram illustrating a zoom button displayed in a stereo measurement mode according to a fourth embodiment of the present invention.

FIG. 12A is a diagram illustrating the zoom button 51, which is an instruction button displayed in a stereo measurement mode. Operation instruction on the left image display region 32 is instructed by a zoom-out operation by pinch-in operation of reducing a distance between the two fingers F4 and F5 on the touch panel or a zoom-in operation by a pinch-out operation of increasing the distance between the two fingers, and when such an operation instruction is received, it is possible to zoom-out or zoom-in the endoscope image by changing the display range of an image being displayed in the left image display region 32 by an amount of variation dg.

The zoom button 51, which is an instruction button, is disposed in a region other than the left image display region 32 where the user performs a pinch-in or pinch-out operation (here, the right image display region 33). That is, in FIG. 12A, the zoom button 51 is disposed superimposed on part of the right image display region 33 so as to cross over a frame line part 54 of the right image display region 33 in the bottom-right corner of the right image display region 33.

Figure 12B:
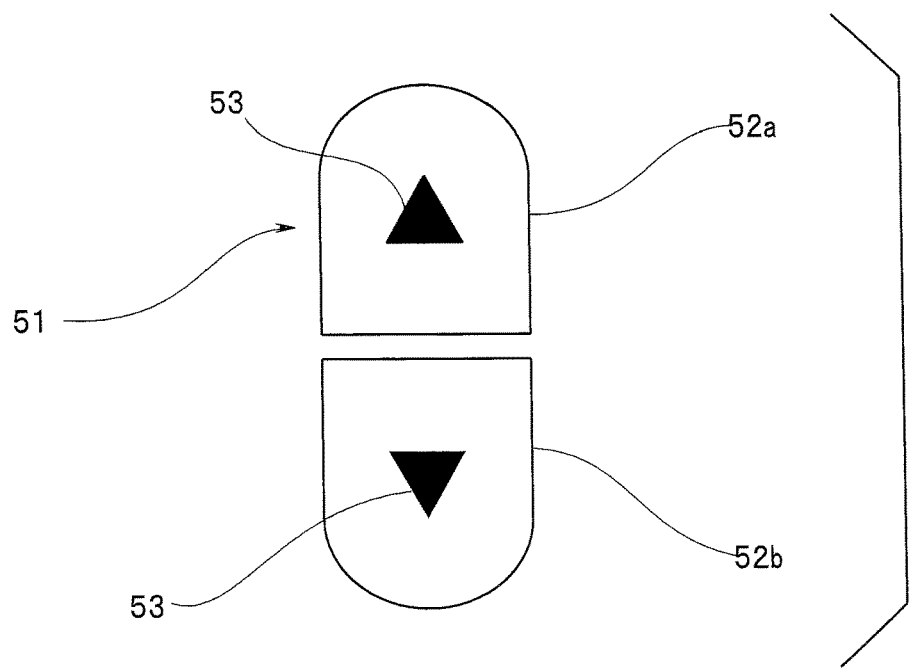
FIG. 12B is an enlarged view of the zoom button according to the fourth embodiment of the present invention.

FIG. 12B is an enlarged view of the zoom button 51. The zoom button 51 is a button on which two ½ elliptical regions constituting an enlargement button 52a and a reduction button 52b respectively are disposed. The two ½ elliptical regions have shapes formed by dividing an ellipse one size smaller than the outer circumference into two parts in a longitudinal direction and each ½ elliptical region includes a small triangular part 53 inside.

The region configured between the enlargement button 52a and the reduction button 52b is transparent so that an image in the right image display region 33 and the frame line part 54 are seen through, while the respective regions of the enlargement button 52a and the reduction button 52b are non-transparent. Therefore, in FIG. 12A, the enlargement button 52a and the reduction button 52b hide the image in the right image display region 33 and the frame line part 54, and the image inside the right image display region 33 and the frame line part 54 are seen through in the region other than the enlargement button 52a and the reduction button 52b.

The enlargement button 52a or the reduction button 52b is a button for instructing to enlarge or reduce the right image display region 33. By touching the enlargement button 52a or the reduction button 52b with the finger, the user can enlarge or reduce the image displayed in the left image display region 32 and the right image display region 33.

That is, the zoom button 51 is an instruction button for instructing to zoom an endoscope image, the enlargement button 52a is a button for instructing to enlarge the endoscope image and the reduction button 52b is a button for instructing to reduce the endoscope image.

With a timer, which is not shown, the zoom button 51 is displayed for a predetermined display time period and hidden after the predetermined display time period elapses.

The ROM 12b stores information of amounts of zoom variations dg and dh.

The amount of zoom variation dg is an amount of variation during zooming within the left image display region 32. Here, the amount of variation dg is an amount corresponding to a change in the distance between the fingers F4 and F5, which are touching the touch panel 14b during a pinch-in or pinch-out operation. That is, the amount of variation dg is defined as a function of an amount of variation in the distance between the fingers F4 and F5 on the touch panel 14b.

The amount of zoom variation dh is an amount of variation during zooming by an operation of the zoom button 51. Here, the amount of variation dh is an amount corresponding to the number of times the enlargement button 52a or the reduction button 52b is touched with the finger or an amount corresponding to each touch. That is, the amount of variation dh is defined as a function of the number of times the enlargement button 52a or the reduction button 52b is touched with the finger. Note that the amount of variation dh may also be defined as a function of a time period during which the enlargement button 52a or the reduction button 52b is touched with the finger.

For example, the amounts of variations dg and dh are defined such that when the user performs a pinch-out operation in the left image display region 32 to change the distance between the fingers F4 and F5 on the touch panel by 1 cm, the display range is enlarged 10 times, and on the other hand, when the user touches the enlargement button 52a once in the right image display region 33, the display range is enlarged 1.1 times.

In this way, the user can perform coarse zooming of zooming the display range in large steps by carrying out a pinch-in or pinch-out operation in the left image display region 32 and fine zooming of zooming the display range in small steps by touching the zoom button 51 of the right image display region 33.

Note that according to the present embodiment, the left image display region 32 is assumed to be the coarse zooming region and the right image display region 33 is assumed to be the fine zooming region, but on the contrary, the left image display region 32 may be assumed as the fine zooming region and the right image display region 33 may be assumed as the coarse zooming region. In that case, when the user touches the right image display region 33, the right image display region 33 is selected as the coarse zooming region and the zoom button 51 for fine-zooming the display range is disposed in a region other than the right image display region 33 (left image display region 32 or the like).

Furthermore, according to the present embodiment, coarse zooming is performed through a pinch-in or pinch-out operation in the left image display region 32 and fine zooming is performed by the zoom button 51 in the right image display region 33, but on the contrary, fine zooming may be performed through a pinch-in or pinch-out operation in the left image display region 32 and coarse zooming may be performed through the zoom button 51 in the right image display region 33. In this case, for example, the amounts of variations dg and dh are defined such that when the user performs a pinch-out operation on the left image display region 32 to change by 1 cm the distance between F4 and F5, the display range is enlarged 1.1 times, and on the other hand, when the user touches the enlargement button 52a in the right image display region 33 once, the display range is enlarged 10 times. According to the configuration, the user can speedily zoom the display range using the enlargement button 52a and accurately zoom the display range through a pinch-in or pinch-out operation.

Figure 13:
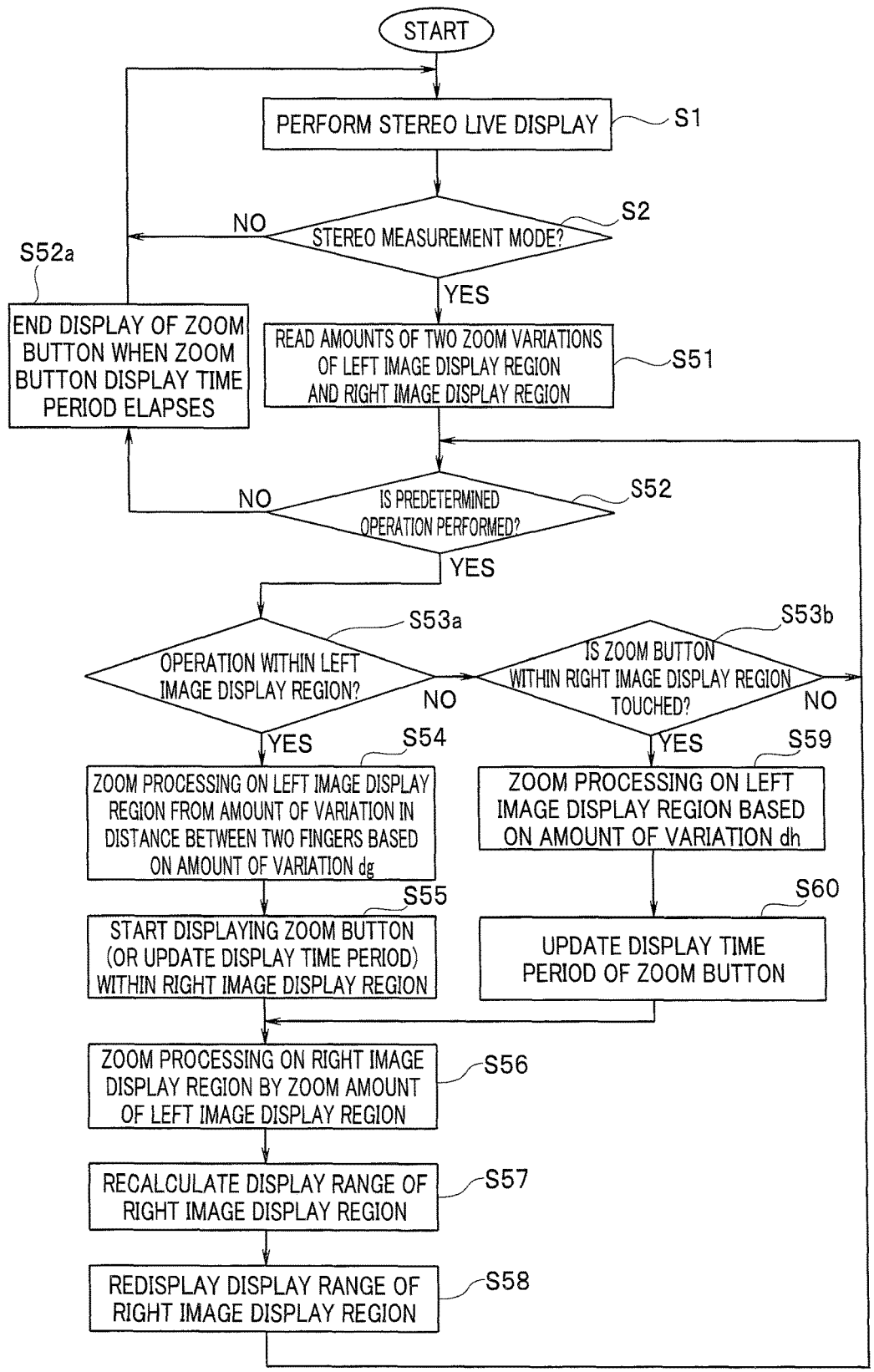
FIG. 13 is a flowchart illustrating a flow example of zoom display processing in the stereo measurement mode according to the fourth embodiment of the present invention.

Next, operation of the endoscope apparatus 1 according to the present embodiment will be described. FIG. 13 is a flowchart illustrating a flow example of zoom display processing in the stereo measurement mode. Note that in FIG. 13, processes identical to the processes in FIG. 3 are assigned identical step numbers and description of the processes is omitted.

When the stereo measurement mode is set (S2: YES), the control section 12 reads information of the amount of variation dg, which is an amount of left eye image zoom variation, and the amount of variation dh, which is an amount of right eye image zoom variation, from the ROM 12B (S51).

The control section 12 determines whether or not a predetermined operation on the touch panel 14b is performed (S52). When no predetermined operation on the touch panel 14b is performed, the process proceeds to S52a. The predetermined operation here is the aforementioned pinch-in or pinch-out operation.

When the process returns to S1 from S52, the control section 12 determines whether or not the zoom button 51 is already displayed, and when the zoom button 51 is already displayed and a predetermined time period elapses after the display of the zoom button 51 is started, the zoom button 51 is hidden (S52a).

More specifically, the process in S52a differs between a case where the zoom button 51 is hidden and a case where the zoom button 51 is already displayed through the process in S55, which will be described later. In S52a, the control section 12 determines whether or not the zoom button 51 is already displayed, and if the zoom button 51 is already displayed and the predetermined display time period of the zoom button 51 elapses, the zoom button 51 is hidden (S52a). After S52a, the process returns to S1.

When a pinch-in or pinch-out operation on the touch panel 14b is performed in S52, the control section 12 determines whether or not the operation is a pinch-in or pinch-out operation within the left image display region 32 (S53a).

When the operation in S53a is a pinch-in or pinch-out operation within the left image display region 32 (S53a: YES), the control section 12 performs zoom processing on the left image display region 32 from an amount of variation in the distance between the two fingers F4 and F5 within the left image display region 32 based on the amount of variation dg (S54). In the case of a pinch-in operation, reduction processing on the left image display region 32 is performed, and in the case of a pinch-out operation, enlargement processing on the left image display region 32 is performed.

Next, the control section 12 performs processing on a display of the zoom button 51, and the processing differs between a case where the zoom button 51 is hidden through initial processing or the like and a case where the zoom button 51 is already displayed through the second and subsequent processes. When the zoom button 51 is hidden due to initial processing or the like, the zoom button is displayed superimposed on and crossing over the frame line part 54 of the right image display region 33 in the bottom-right corner of the right image display region 33. When the zoom button 51 is already displayed through the second and subsequent processes, the display time period is updated so as to be extended (S55).

After the process in S55, the control section 12 zooms the right image display region 33 by a zoom amount of the left image display region 32 (S56). As a result, the right image display region 33 is also zoomed by the same amount as the amount of the left image display region 32.

After zooming the right image display region 33, the control section 12 recalculates the display range of the right image display region 33 corresponding to the display range of the left image display region 32 through matching processing (S57).

After S57, the control section 12 redisplays the display range of the right image display region 33 corrected by the recalculation (S58).

Note that the display range of the right image display region 33 is recalculated after zooming the right image display region 33 (S56), but the right image display region 33 may also be zoomed while correcting the display range of the right image display region 33 through the recalculation in S56.

After S58, the process returns to S52.

When the operation in S53a is not a pinch-in or pinch-out operation within the left image display region 32 (S53a: NO), the control section 12 further determines whether or not the operation in S53a is a touch operation on the enlargement button 52a or the reduction button 52b on the zoom button 51 of the right image display region 33 (S53b). When the operation in S53b is not the touch operation on the enlargement button 52a or the reduction button 52b of the right image display region 33 (S53b: NO), the process returns to S52.

On the other hand, when the operation in S53b is a touch operation on the enlargement button 52a or the reduction button 52b of the right image display region 33 (S53b: YES), the process proceeds to S59.

The control section 12 determines which of the enlargement button 52a or the reduction button 52b is touched, and enlarges the display range of the left image display region 32 when the enlargement button 52a is touched or reduces the left image display region 32 when the reduction button 52b is touched, based on the amount of variation dh (S59).

After the zoom button 51 of the right image display region 33 is touched, the control section 12 updates the display time period of the zoom button 51 so as to be extended (S60).

After S60, the process proceeds to S56.

The processing in FIG. 13 ends when the user instructs to end the stereo measurement processing mode on the menu screen.

As described above, the processes in S54 to S60 constitute a display control section that performs display control such that while the left image display region 32 is selected, if an operation instruction for a zoom operation such as a pinch-in or pinch-out operation is received, the display range of the left image display region 32 and the right image display region 33 is changed by the amount of variation dg, and while the right image display region 33 is selected, if an operation instruction such as a touch operation of the zoom button 51 is received, the display range of the left image display region 32 and the right image display region 33 is changed by the amount of variation dh which is different from the amount of variation dg.

In the aforementioned example, the amount of variation dg is set to be greater than the amount of variation dh, and so by repeating the processing in FIG. 13, the user can repeat coarse zooming of changing the display range of the left image display region 32 and the display range of the right image display region 33 in large steps by performing a pinch-in or pinch-out operation within the left image display region 32, and fine zooming of changing the display range of the left image display region 32 and the display range of the right image display region 33 in small steps by touch operation of the zoom button 51 of the right image display region 33, one or more times respectively. Thus, the user can zoom the display range of the left image display region 32 and the display range of the right image display region 33 in a desired size speedily and accurately.

Next, modifications of the aforementioned four embodiments will be described.

(Modification 1)

With the endoscope apparatus 1 according to the aforementioned first embodiment and third embodiment, only measurement points can be specified, but it may also be possible to allow the zoom display processing according to the second embodiment to be performed simultaneously.

When specifying a measurement point, the user may want to check a region to be measured after zooming out the endoscope image once or specify a measurement point after zooming in and enlarging the endoscope image.

Thus, it may also be possible to allow the endoscope apparatus 1 to perform both the cursor display processing according to the aforementioned first embodiment or the third embodiment and the zoom processing according to the second embodiment or the zoom processing according to the fourth embodiment.

Note that in such a case, it may also be possible to change the amounts of variations da, db, de and df depending on the zoom amount of the endoscope image.

(Modification 2)

In the four aforementioned embodiments, cursor display processing or zoom processing is executed in the stereo measurement mode, but the aforementioned cursor display processing or zoom processing may be executed even when the same endoscope image is displayed in the two image display regions in other modes except the stereo measurement mode. The modification is also convenient, for example, when a certain point is specified speedily and accurately on the same endoscope image or a certain point is marked speedily and accurately or zooming is performed speedily and accurately.

(Modification 3)

In the four aforementioned embodiments, the endoscope apparatus 1 displays two image display regions on the display section 14, but the endoscope apparatus 1 may also be configured to display three or more image display regions. In that case, an amount of variation of the cursor and an amount of variation during zooming differ among a plurality of image display regions.

In addition to the aforementioned left image display region 32 and the right image display region 33, when a third image display region is displayed, if a display magnification of the third image display region is different from the display magnifications of the left image display region 32 and the right image display region 33, a moving amount or a zoom amount at a point in the third image display region is different from the moving amount or zoom amount at a point in the left image display region 32 and the right image display region 33.

(Modification 4)

The four aforementioned embodiments use a touch panel for the aforementioned cursor movement operation and zoom operation, but the measurement point specification operation may be performed using the joystick of the operation section 15 and the zoom operation may be performed using the zoom operation button provided at the operation section 15. The joystick can specify a direction according to a direction toward which the joystick is tilted.

It has been stated in the aforementioned first embodiment that when the cursor 35a on the left image display region 32 is dragged, if the finger F may move beyond the left image display region 32 or when the cursor 35*b* on the right image display region 33 is dragged, if the finger F moves beyond the right image display region 33, when a drag operation is performed beyond the image display region first touched with the finger F, the cursors 35*a* and 35*b* may be moved by continuously using the value of an amount of variation for the image display region first touched with the finger F.

When the joystick in the present modification 4 is used, if a tilting operation is performed beyond the image display region when the joystick tilting operation starts, the cursors 35*a* and 35*b* are moved by continuously using the value of an amount of variation for the image display region when the tilting operation starts.

(Modification 5)

The four aforementioned embodiments may also be configured such that the cursor 35*a* moves in large steps or a zoom amount is large in the left image display region 32, the cursor 35*b* moves in small steps or a zoom amount is small in the right image display region 33, whereas the cursor 35*a* moves in small steps or the zoom amount is small in the left image display region 32 and the cursor 35*b* moves in large steps or the zoom amount is large in the right image display region 33.

(Modification 6)

According to the four aforementioned embodiments, the positions of the left image display region 32 and the right image display region 33 on the LCD 14*a* are fixed, but the positions of the left image display region 32 and the right image display region 33 may be reversed or made recoverable. That is, the left and right positions of the two image display regions 32 and 33 may be interchanged on the LCD 14*a* of the display section 14 according to a predetermined operation.

For example, two inspectors facing each other may view an image displayed on one display section of the endoscope apparatus. Thus, some endoscope apparatuses allow the orientation of the screen of the display section to be changed by 180 degrees (that is, reversed). In such endoscope apparatuses, when the orientation of the screen of the display section is changed by 180 degrees (that is, reversed), the vertical direction of the screen of the display section is reversed.

Thus, when the orientation of the screen of the display section is reversed, the left and right image display regions may be made interchangeable.

(Modification 7)

In the four aforementioned embodiments, data of each amount of variation da, db, dc, dd, df, dg or dh is stored in the ROM 12*b*, but such data may also be stored in a memory card or the like and may be read via the memory card I/F 17. If the memory card is a rewritable memory such as a flash memory, it may be possible to allow the user to change the value of each amount of variation da, db, dc, dd, df, dg or dh.

(Modification 8)

In the aforementioned third embodiment, the move button is displayed by touching the right image display region or the left image display region, and hidden after a predetermined time period elapses, but a configuration may also be provided which includes a switching button for displaying or not displaying the move button. According to the configuration, the user can freely switch between display and non-display of the move button, improve operability of the move button and consequently specify positions such as a measurement point in an endoscope image speedily by a small number of operations. Furthermore, even when switching is performed so as to display the move button, the move button is automatically hidden during a touch operation so that the move button does not obstruct the movement.

(Modification 9)

In the aforementioned fourth embodiment, the zoom button is displayed by touching the right image display region or the left image display region, and hidden after a predetermined time period elapses, but a configuration may also be provided which includes a switching button for displaying or not displaying the zoom button. According to the configuration, the user can freely switch between display and non-display of the zoom button, improve operability of the zoom button and consequently change the display range of the endoscope display speedily by a small number of operations. Furthermore, even when switching is performed so as to display the zoom button, the zoom button is automatically hidden during a touch operation so that the zoom button does not obstruct the operation.

(Modification 10)

Although the four aforementioned embodiments have been described by taking an endoscope apparatus as an example, the aforementioned respective embodiments are also applicable to a case where two image display regions are displayed for an endoscope image recorded in an apparatus such as a personal computer to specify a measurement point and enlarge or reduce a display range as described above. In that case, the apparatus such as a personal computer constitutes an endoscope image display apparatus.

Each "section" in the present specification is a conceptual one corresponding to each function in each embodiment and does not necessarily have a one-to-one correspondence with a specific hardware or software routine. Order of execution of steps of each procedure in each embodiment may be changed unless contrary to the nature of the procedure, a plurality of steps may be executed simultaneously or steps may be executed in different order every time the steps are executed. Furthermore, all or some steps of each procedure in each embodiment may be implemented by hardware.

The present invention is not limited to the aforementioned embodiments, but various changes, modifications or the like can be made within the scope without changing the spirit of the present invention.

According to the present invention, it is possible to provide an endoscope image display apparatus, an endoscope image display method and an endoscope image display program that can specify a position such as a measurement point in at least two or more endoscope images or change a display range of an endoscope image displayed on a screen speedily by a small number of operations.

What is claimed is:

1. An endoscope image display apparatus comprising:
   a display apparatus comprising a first image display region and a second image display region configured to display an endoscope image;
   a selection section configured to select one of the first image display region and the second image display region; and
   a display control section configured to perform display control so as to change, upon receiving a first operation instruction while the first image display region is selected by the selection section, a position of a mark or a display range of an image displayed in the first image display region and the second image display region, by a first amount of variation, and change, upon receiving a second operation instruction while the second image display region is selected by the selection section, the position of the mark or the display range of the image displayed in the first image display region and the second image display region, by a second amount of variation which is different from the first amount of variation.

2. The endoscope image display apparatus according to claim 1, wherein a first endoscope image displayed in the first image display region and a second endoscope image displayed in the second image display region have parallax with respect to each other.

3. The endoscope image display apparatus according to claim 2, wherein the first endoscope image and the second endoscope image are left and right endoscope images for stereo measurement.

4. The endoscope image display apparatus according to claim 1, wherein the display control section performs the display control when an endoscope apparatus enters a stereo measurement mode.

5. The endoscope image display apparatus according to claim 1, wherein a first endoscope image displayed in the first image display region and a second endoscope image displayed in the second image display region are identical images.

6. The endoscope image display apparatus according to claim 1, wherein the display apparatus comprises a touch panel, and
the first operation instruction and the second operation instruction are instructions given by touching the touch panel.

7. The endoscope image display apparatus according to claim 1, further comprising an operation section that can specify a direction,
wherein the first operation instruction and the second operation instruction are specifications of the direction by the operation section.

8. The endoscope image display apparatus according to claim 7, wherein the operation section is a joystick.

9. The endoscope image display apparatus according to claim 1, wherein the display control section continuously changes, when the first operation instruction given while the first image display region is selected remains in progress even in a region beyond the first image display region, the position of the mark based on the first amount of variation, and continuously changes, when the second operation instruction given while the second image display region is selected remains in progress even in a region beyond the second image display region, the position of the mark based on the second amount of variation.

10. The endoscope image display apparatus according to claim 1, wherein the second operation instruction is given by an instruction button disposed in a region other than the first image display region.

11. The endoscope image display apparatus according to claim 10, wherein display or non-display of the instruction button can be switched.

12. The endoscope image display apparatus according to claim 11, wherein the instruction button is displayed when the first operation instruction is given during the non-display.

13. The endoscope image display apparatus according to claim 10, wherein the instruction button is hidden after a predetermined display time period elapses after the second operation instruction is given.

14. The endoscope image display apparatus according to claim 10, wherein the instruction button is hidden when an instruction to determine the position is given.

15. The endoscope image display apparatus according to claim 10, wherein the instruction button comprises a button configured to instruct a movement.

16. The endoscope image display apparatus according to claim 10, wherein the instruction button is displayed at a position that does not obstruct the mark.

17. The endoscope image display apparatus according to claim 15, wherein the first amount of variation is an amount of difference between a position indicated by the first operation instruction and the position of the mark displayed in the first image display region, and
when the first operation instruction is received, the position of the mark displayed in the first image display region is changed to the position indicated by the first operation instruction.

18. The endoscope image display apparatus according to claim 10, wherein the instruction button comprises a button configured to instruct zooming.

19. The endoscope image display apparatus according to claim 18, wherein the first operation instruction is given by a zoom-out operation by a pinch-in operation of reducing a distance between two fingers on the touch panel or a zoom-in operation by a pinch-out operation of increasing the distance between the two fingers, and
when the first operation instruction is received, the display range of the image displayed in the first image display region is changed by the first amount of variation.

20. The endoscope image display apparatus according to claim 1, wherein when or after the position of the mark or the display range of the image is changed, the display control section recalculates the position of the mark or the display range of the image through matching processing.

21. The endoscope image display apparatus according to claim 1, wherein the endoscope image display apparatus is an endoscope apparatus.

22. An endoscope image display method comprising:
selecting, in a display apparatus comprising a first image display region and a second image display region configured to display an endoscope image, one of the first image display region and the second image display region; and
performing display control so as to change, upon receiving a first operation instruction while the first image display region is selected, a position of a mark or a display range of an image displayed in the first image display region and the second image display region, by a first amount of variation, and change, upon receiving a second operation instruction while the second image display region is selected, the position of the mark or the display range of the image displayed in the first image display region and the second image display region, by a second amount of variation which is different from the first amount of variation.

23. An endoscope image display program in a display apparatus comprising a first image display region and a second image display region configured to display an endoscope image, the program being configured to display the first image display region and the second image display region, the program causing a computer to carry out:
a function of selecting one of the first image display region and the second image display region; and
a function of performing display control so as to change, upon receiving a first operation instruction while the first image display region is selected, a position of a mark or a display range of an image displayed in the first image display region and the second image display region, by a first amount of variation in the first image display region, and change, upon receiving a second operation instruction while the second image display region is selected, the position of the mark or the display range of the image displayed in the first image display region and the second image display region, by a second amount of variation which is different from the first amount of variation in the second image display region.

* * * * *